US006534298B2

(12) United States Patent
Taylor et al.

(10) Patent No.: US 6,534,298 B2
(45) Date of Patent: Mar. 18, 2003

(54) NUCLEIC ACIDS ENCODING α-1,3 FUCOSYLTRANSFERASES AND EXPRESSION SYSTEMS FOR MAKING AND EXPRESSING THEM

(75) Inventors: Diane E. Taylor, Edmonton (CA); Zhongming Ge, Edmonton (CA)

(73) Assignee: The Govenors of the University of Alberta, Edmonton (CA)

( * ) Notice: Subject to any disclaimer, the term of this patent is extended or adjusted under 35 U.S.C. 154(b) by 0 days.

(21) Appl. No.: 09/733,524

(22) Filed: Dec. 7, 2000

(65) Prior Publication Data

US 2002/0068347 A1 Jun. 6, 2002

Related U.S. Application Data

(62) Division of application No. 09/092,315, filed on Jun. 5, 1998, now Pat. No. 6,399,337.
(60) Provisional application No. 60/048,857, filed on Jun. 6, 1997.

(51) Int. Cl.[7] .......................... C12N 9/10; C12N 15/54
(52) U.S. Cl. .................... 435/193; 435/320.1; 435/325; 435/254.2; 435/254.11; 435/419; 435/252.3; 536/23.1
(58) Field of Search ................ 536/23.2, 23.1; 435/193, 320.1, 325, 252.3, 419, 254.11, 254.2

(56) References Cited

U.S. PATENT DOCUMENTS 5,324,663 A * 6/1994 Lowe ...................... 435/320.1

OTHER PUBLICATIONS

GenBank Accession No. AE000554. Aug. 6, 1997.*
GenBank Accession No. AE000578. Aug. 6, 1997.*
J. Costa et al., "Stable Expression of the Golgi Form and Secretory Variants of Human Fucosyltransferase III From BHK–21 Cells", J. Biol. Chem. 272(17): 11613–11621. Apr. 25, 1997.*
Warren, J. R., and Marshall, B. J. (1983) Lanceti, 1273–1275.
Graham, G. Y. (1991) *J. Gastroenterol. Hepatol.* 6, 105–113.
Parsonnet, J. et al., (1991) *N. Ensl. J. Med.* 325, 1127–1131.
Forman, D. et al., (1993) *Lancet* 341, 1359–1362.
Nakamura, S. et al., (1997) *Cancer* 79, 3–11.
Wirth, H.–P. et al., (1996) *Infect. Immun.* 64, 4598–4605.
Feizi, T. (1985) *Nature* 314, 53–57; Muramatsu, T. (1988) *Biochemie* 70, 1587–1596.
Hakomori, S. (1989) *Adv. Cancer Res.* 52, 257–331.

Sherburne, R., and Taylor, D. E. (1995) *Infect. Immun.* 63, 4564–4568.
Weston, B. W., Smith, Kelly, R. J., and Lowe, J. B. (1992) *J. Biol. Chem.* 267, 24575–24584.
Gersten, K. M. et al., (1995) *J. Biol. Chem.* 270, 25047–25056.
Chan, N. W. C. et al., (1995) *Glycobiology* 5, 683–688.
Hitoshi, S., Kusunoki, S., Kanazawa, I., and Tsuji, S. (1996) *J. Biol. Chem.* 271, 16975–16981.
Goelz et al., (1990) *Cell* 63, 1349–1376.
Kukowska–Latallo, J. F., Larson, R. D., Nair, R. P., and Lowe, J. B. (1990) *Genes & Dev.* 4, 1288–1303.
Lowe et al., (1991) *J. Biol. Chem.* 266, 17467–17477.
Kumar, R., Potvin, B., Muller, W. A., and Stanley, P. (1991) *J. Biol. Chem.* 266, 21777–12783.
Weston, B. W., J. F., Nair, R. P., Larson, R. D., and Lowe, J. B. (1992) *J. Biol. Chem.* 267, 4152–4160.
Koszdin, K. L., and Bowen, B. R. (1992) *Biochem. Biophys. Res. Commun.* 187, 152–157.
Sasaki et al., (1994) *J. Biol. Chem.* 269, 14730–14737.
Natsuka, S., Gersten, K. M., Zenita, K., Kannagi, R., and Lowe, J. B. (1994) *J. Biol. Chem.* 269, 16789–16794.
Lee et al., (1996) *J. Biol. Chem.* 271, 32960–32967.
Tomb, J.F. et al., "Tfucosyltransferase of *Helicobactor Pylori*" EMBL database entry 025366, ascension No. 025366, Jan. 1, 1998 (see abstract only).
Tomb, J.F. et al., "The complete genome sequence of the gastric pathogen *Helicobacter pylori*" Nature, vol. 388, Aug. 1997, pp. 539–547.
Joziasse, D. H. (1992) *Gycobiology* 2, 217–277.
Paulson, S., and Colley, K. J. (1989) *J. Biol. Chem.* 264(30), 17615–17618.
Kelly, M. M., Phanhthourath, C., Brees, D. K., McCabe, C. F., and Cole, G. J. (1995) *Dev. Brain Res.* 85, 31–47.
Peterson, W. I. (1991) *N. Engl. J. Med.* 324, 1043–1048.
Martin et al. (1997) *J. Biol. Chem.* 272 (34) 21349–21356.
Ge et al. (1997) *J. Biol. Chem.* 272 (34), 21357–21363.
Muramatsu, T. (1988) *Biochimie* 70, 1587–1596.

* cited by examiner

*Primary Examiner*—Rebecca E. Prouty
(74) *Attorney, Agent, or Firm*—Fish & Richardson P.C.

(57) ABSTRACT

A bacterial α1,3-fucosyltransferase gene and deduced amino acid sequence is provided. The gene is useful for preparing α1,3-fucosyltransferase polypeptide, and active fragment thereof, which can be used in the production of oligosaccharides such as Lewis X, Lewis Y, and siayl Lewis X, which are structurally similar to certain tumor-associated carbohydrate antigens found in mammals. These product glycoconjugates also have research and diagnostic utility in the development of assays to detect mammalian tumors. In addition the polypeptide of the invention can be used to develop diagnostic and research assays to determine the presence of *H. pylori* in human specimens.

22 Claims, 12 Drawing Sheets

```
1
TCTGGCTTGCACAGCTATGCCGCAGGCGATCCCTTGCCGATCCCTACTTTCTTATACTTT
    ZGE37

Inverted repeat
TTGGTAGCGATACCTTTTGCTCTTGTGATCTTGGCGTATTTTAAACGCCATTTGAGTTTG
             -35                        -10
121              .Kozak box.
CCTAAATTGGTTTAAAGGATAACCATGTTCCAACCCCTATTAGACGCTTATGTAGAAAGC
                SD        M F Q P L L D A Y V E S GCTTCCATTGAAAAAATGGCCTCTAAATCTCCCCCCCCCCTAAAAATCGCTGTGGCGAAT
 A S I E K M A S K S P P P L K I A V A N
241
TGGTGGGGAGATGAAGAAATTAAAGAATTTAAAAATAGCGTTCTTTATTTTATCCTAAGC
 W W G D E E I K E F K N S V L Y F I L S CAACGCTACACAATCACCCTCCACCAAAACCCCAATGAATTTTCAGATCTCGTCTTTGGT
 Q R Y T I T L H Q N P N E F S D L V F G
361
AACCCCCTTGGATCGGCCAGAAAAATCTTATCCTATCAAAACGCTAAACGAGTGTTTTAC
 N P L G S A R K I L S Y Q N A K R V F Y ACCGGTGAAAACGAATCGCCTAATTTCAACCTCTTTGATTACGCCATAGGCTTTGATGAA
 T G E N E S P N F N L F D Y A I G F D E
481
TTGGATTTTAATGATCGTTATTTGAGAATGCCTTTATATTATGATAGGCTACACCATAAA
 L D F N D R Y L R M P L Y Y D R L H H K GCCGAGAGCGTGAATGACACCACTGCGCCCTACAAACTCAAAGATAACAGCCTTTATGCT
 A E S V N D T T A P Y K L K D N S L Y A
601
TTAAAAAAACCCTCCCATTGTTTTAAAGAAAAACACCCCAATTTATGCGCAGTAGTGAAT
 L K K P S H C F K E K H P N L C A V V N GATGAGAGCGATCCTTTGAAAAGAGGGTTTGCGAGCTTTGTCGCGAGCAACCCTAACGCC
 D E S D P L K R G F A S F V A S N P N A
721
CCTATAAGGAACGCTTTCTATGACGCTCTAAATTCTATTGAACCAGTTACTGGGGGAGGG
 P I R N A F Y D A L N S I E P V T G G G AGCGTGAGAAACACTTTAGGCTATAACGTCAAAAACAAAAACGAGTTTTTAAGCCAATAC
 S V R N T L G Y N V K N K N E F L S Q Y
841
AAGTTCAACCTGTGTTTTGAAAACACTCAAGGCTATGGCTATGTAACTGAAAAAATCATT
 K F N L C F E N T Q G Y G Y V T E K I I GACGCTTACTTTAGCCATACCATTCCTATTTATTGGGGGAGTCCTAGCGTGGCGAAAGAT
 D A Y F S H T I P I Y W G S P S V A K D
961
TTTAACCCTAAAAGTTTTGTGAATGTGCATGATTTCAAAAACTTTGATGAAGCGATTGAC
 F N P K S F V N V H D F K N F D E A I D TATATCAAATACTTGCACACGCACAAAAACGCTTATTTAGACATGCTTTATGAAAACCCT
 Y I K Y L H T H K N A Y L D M L Y E N P
```

FIG. 2A-1

```
1081             .              .              .              .              .
TTGAACACCCTTGATGGGAAAGCTTACTTTTACCAAAATTTGAGTTTTAAAAAGATCCTA
 L  N  T  L  D  G  K  A  Y  F  Y  Q  N  L  S  F  K  K  I  L

.              .              .              .              .
GCTTTTTTTAAAACGATTTTAGAAAACGATACGATTTATCACGATAACCCTTTCATTTTC
 A  F  F  K  T  I  L  E  N  D  T  I  Y  H  D  N  P  F  I  F
1201      .  ZGE38  .              .              .              .
TGTCGTGATTTGAATGAGCCTTTAGTAACTATTGATGATTTGAGGGTTAATTATGATGAT
 C  R  D  L  N  E  P  L  V  T  I  D  D  L  R  V  N  Y  D  D

.              .              .              .              .
TTGAGGGTTAATTATGATGATTTGAGAATTAATTATGATGATTTGAGGGTTAATTATGAT
 L  R  V  N  Y  D  D  L  R  I  N  Y  D  D  L  R  V  N  Y  D
1321             .              .              .              .
GATTTGAGGGTTAATTATGATGATTTGAGAATTAATTATGATGATTTGAGGGTTAATTAT
 D  L  R  V  N  Y  D  D  L  R  I  N  Y  D  D  L  R  V  N  Y

.              .              .              .              .
GATGATTTGAGGGTTAATTATGAGCGCCTCTTATCAAAAGCTACCCCTCTTTTGGAATTA
 D  D  L  R  V  N  Y  E  R  L  L  S  K  A  T  P  L  L  E  L
1441             .              .              .              .              .
TCCCAAAACACCACTTCTAAAATCTATCGCAAAGCTTACCAAAAATCCTTACCTTTGTTG
 S  Q  N  T  T  S  K  I  Y  R  K  A  Y  Q  K  S  L  P  L  L

.              .              .              .     Stem loop .
CGCGCCATAAGGAGATGGGTTAAAAAATTGGGTTTGTAAAATTGGGGGTAAACTAAACCC
 R  A  I  R  R  W  V  K  K  L  G  L  *  .       CCCCATTTGATTTGGG
                                                          *  V
1561             .              .              .              .
CTTGCGCTATCATCGCAGACGCTACTTTTCTAAAACCAGCGATATTAGCCCCTAA
GAACGCGATAGTAGCGTCTGAGATGAAAAGATTTTGGTCGCTATAATCGGGGATT
 G  Q  A  I  M  A  S  A  V  K  R  F  G  A  I  N  A  G  L .              .              .              .  ZGE39  .
AACAAAATTAGTAGGGTCTTTAAACTCTTTAGCGGTTTGAGAGACATTCTTATAA
TTGTTTTAATCATCCCAGAAATTTGAGAAATCGCCAAACTCTCTGTAAGAATATT
   V  F  N  T  P  D  K  F  E  K  A  T  Q  S  V  N  K  Y
C-terminal sequence of the putative glutamate dehydrogenase
```

Fig. 2A-2

```
BFucT3   ..........  ..........  ..........  ..........  ..........  ..........  ..........  ..........
HFucT6   ..........  ..........  ..........  ..........  ..........  ..........  ..........  ..........
MFucT4   MAPARQELQH  ESRCRPSRTV  DAWRAAVATR  GRHMETPGYR  RRTRCGGWGL  PR.SVSSLAA  VGLLC.....  ..........
CFucT1   ..........  ..........  ..........  .....MEL    GPRWSPAA..  ......RPGCP RRWR......  .R.RWALLGA
HpFucT1  ..........  ..........  ..........  ..........  ..........  ..........  ..........  ..........

MYPPGCA  KVKCSWHHCL  PGLLLQLILA  LCFFSYLRMS  QEKPKPKPMW  VSELGAPSQA  TEGSSAHLPL
                                                           MDPLGPA  KPQWSWRCCL  TTLLFQLIMA  VCFFSYLRVS  QDDPT.....  VYPNGSRFPD  STGTPAHSIP
                                                                                                       .....TALTTF ICWGQLPPLP  WASPAPQRLV
                                                                                           ...LLG..    ...AALALY   VCVRELRRRG  SAAGRPEGEV
                                                           ...MFQPLLD AYVESASIEK  MASKSPPPLK IAVANWWGDE  EIKEFKNSVL

BFucT3   RVLLWTWPFN  QPVALSRC..  .SELMPGTAD  CQLTVNRS..  EYPQADAVFV  HHREVS..HR  PKMQLPPSP.  ..........
HFucT6   LILLWTWPFN  KPIALPRC..  .SEMVPGTAD  CNITADRK..  VYPQADAVIV  HHREVM..YN  PSAQLPRSP.  ..........
MFucT4   GVLLWWEPFR  GRGGYPKSPP  DCSLRFNISG  CRLLTDRA..  AYGEAQAVLF  HHRDLVKELH  DWPP.PWGAR  ERTDKALVLR  VFDDQEGAVT  LTGKALETVK
CFucT1   TVLLWWEPF.  ...GRPWRPA  DCRRRYNITG  CLLSADRG..  RYGEARAVLF  HHRDL..ALH  GRQGLPRGP.  ..........
HpFucT1  YFILS.....  QRYTITLHQN  PNEFSDLVFG  NPLGSARKIL  SYQNAKRVFY  TGENESPNFN  ..........  ..........  ..........  .LFDYAIGFD

BFucT3   .RPADQRWVW  FSMESPSNCL  KLKDLD.GYF  NLTMSYRRDS  DIFMPYGWLE  PWP...SQPV  ETLLNI....  .SAKTKLVAW  VVSNWNTDSI  RVQYYKLLKP
HFucT6   .RRQGQRMIW  FSMESPSHCW  QLKAMD.GYF  NLTMSYRSDS  DIFTPYGWLE  PWS...GQPA  HPPLNL....  .SAKTELVAW  AVSNWGPNSA  RVRYYQSLQA
MFucT4   SRPPGQRWVW  MNFESPSHTP  GLRGLAKDLF  NWTLSYRTDS  DVFVPYGFLY  SRSDPTEQPS  GLGPQL....  .ARKRGLVAW  VVSNWNEHQA  RVRYYHQLSR
CFucT1   PRPPGQRMVW  MNFESPSHSP  GLRGLA.GLF  NWTMSYRRDS  DVFVPYGYLY  ......EPPS  PRPFVL....  .PRKSRLVAW  VISNWNEEHA  RVRYYRQLKE
HpFucT1  ELDFNDRYLR  MPL....YYD  RLHHKAESVN  DTTAPYKLKD  NSL..YALKK  PSHCFKEKHP  NLCAVNDES   DPLKRGFASF  VASNPNA.PI  RNAFYDALNS
                                                                                                      →  The conserved region BFucT3   HLQVDVYGRF  HT..PLPHAL  MAKQLSQYKF  YLAFENSLHP  DYITEKLWKN  ALQAMAVPVV  LGPSRVNYEQ  FLPPKAFIHV  EDFQSPKDLA  QYLLALDKDY
HFucT6   HLKVDVYGRS  HK..PLPQGT  MMETLSRYKF  YLAFENSLHP  DYITEKLWRN  ALEAWAVPVV  LGPSRSNYER  FLPPDAFIHV  DDFQSPKDLA  RYLQELDKDH
MFucT4   HVSVDVFGRT  GPGRPVPAIG  LLHTVARYKF  YLAFENSRHV  DYITEKLWRN  AFLAGAVPVV  LGPDRANYER  FVPRGAFIHV  DDFNAASLA   AYLLFLDRNV
CFucT1   HLPIDVYG..  ARGMALLEGS  VVKTVSAYKF  YLAFENSQHT  DYITEKLWKN  AFAASAVPVV  LGPRRANYER  FIPADSFIHV  DDFPSPRLLA  TYLKFLDKNK
HpFucT1  IEPVTGGGSV  RNTLGYNVKN  KNEFLSQYKF  NLCFENTQGY  GVVTEKI.ID  AYFSHTIPIY  WGSPSVAKD.  .FNPKSFVNV  HDFKNFDEAI  DYIKYLHTHK
```

*Fig. 3A-1*

```
BFucT3   A..........  ..........  ..........  ..........  .....SYLNY FRWRETLRPR SFS.WALMFC KACWKLQ.QE PRYQTVPSIA SWFQ  end  356
HFucT6   A..........  ..........  ..........  ..........  .....RYLSY FRWRETLRPR SFS.WALAFC KACWKLQ.EE SRYQT.RGIA AWFT  end  359
MFucT4   A..........  ..........  ..........  ..........  .....VYRRY FRWRRSFAVH ITSFWDEQWC RTCQAVQTSG DQPKSIHNLA DWFQR end  433
CFucT1   P..........  ..........  ..........  ..........  .....SYRRY FAWRNKYEVH VTSFWDEHYC KVCEAVRTAG NQLKTVQNLA GWFES end  356
HpFucT1  NAYLDMLYEN   PLNTLDGKAY  FYQNLSFKKI  LAFFKTILEN  DTIYHDNPFI .FCRDL...N EPLVTIDDLR VNYDD                          372
                                                                   *
```

Fig. 3A-2

```
                                       Sequence comparison with HpFucT
                                       Identity      Similarity
HpFucT    (394) LRVNYDDLRINYDDLRVNYERLLSKRTPL  (429)
EAP-300   (908) LQVEHEDLQVEHGDLQEEHGDLQVEHEDLQVEHGDL (943)     33%            61%
         (1061) LQEEHGDLQEEHGDLQVEHEDLQVEHGDL (1096)           30%            58%
ATHB-6    (119) LEKDYGVLKTQYDSLRHNFDSLRRDNESLLQEISKL (154)     41%            58%
ATHB-7     (78) LETEYNILRQNYDNLASQFESLKKEKQALVSELQRL (113)     32%            54%
TAFT1     (222) LAIQVQSLTAENNTLKSEINKLMENSEKLKENAAL (257)
CPRF1     (301) LAIKVDSLTAENMALKAEINRLTLTAEKLTNDNSRL (336)
TodS       (36) ARIIFDGLYEFVGLLDAHGNVLEVNQVALEGGGITL (71)
```

Fig. 3B

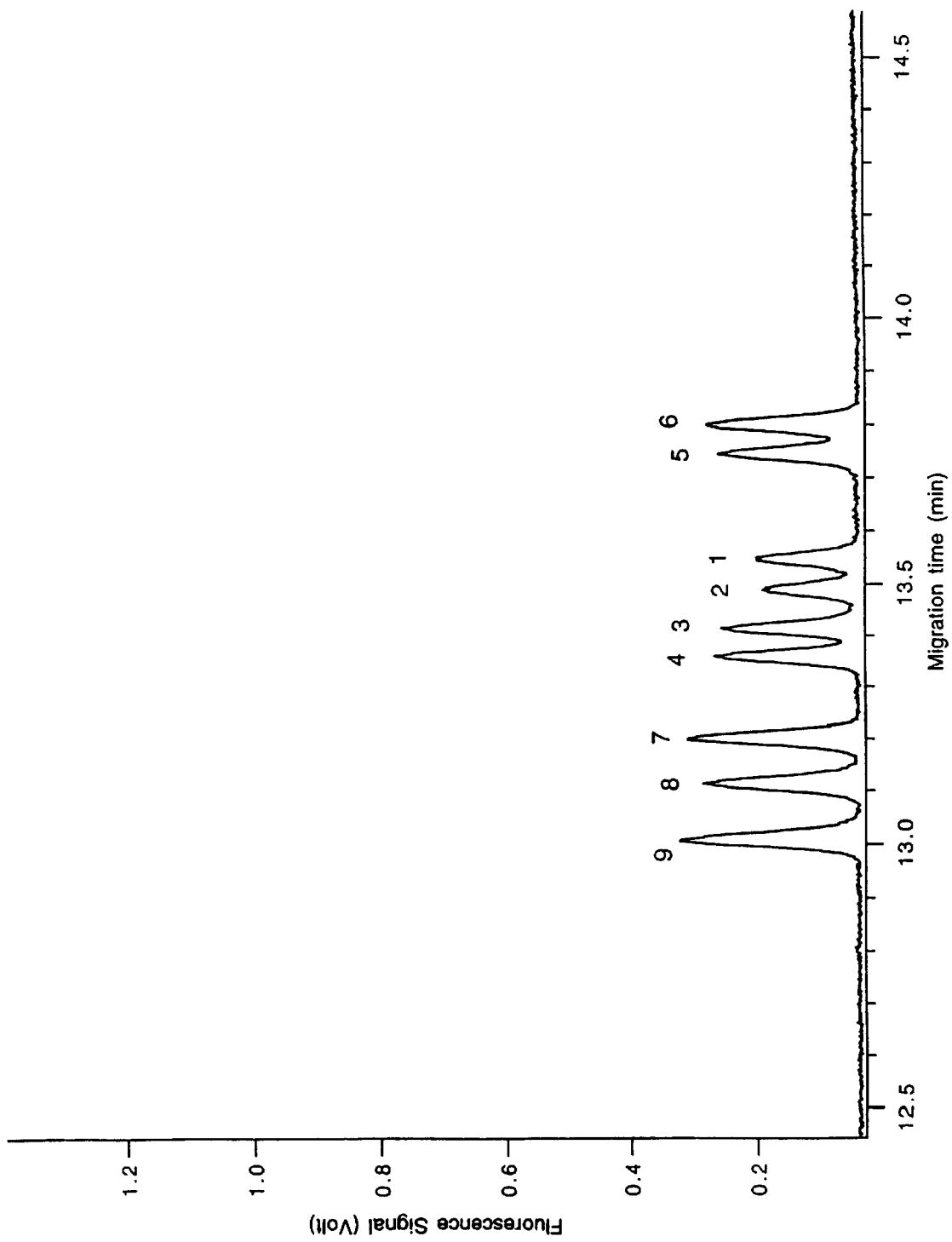

```
26695A   MFQPLLDAFIESASIEKMVSKSPPPPLKIAVANWWGDEEIKEFKKSVLYFILSQRYAITL
26695B   MFQPLLDAFIESASIEKMASKSPPPPLKIAVANWWGDEEIKEFKKSVLYFILSQRYAITL
1182     MFQPLLDAYIESASIEKITSKS-PPPLKIAVANWWGDEEVEEFKKNILYFILSQHYTITL
763      MFQPLLDAYVESASIEKMASKS-PPPLKIAVANWWGDEEIKEFKNSVLYFILSQRYTITL
11637    MFQPLLDAFIESASIEKMASKS-PPPLKIAVANWWGDEEIKEFKKSTLYFILSQHYTITL
                          ↑
802      MFQPLLDAFIESASIKKMPLSY--PPPLKIAVANWWGGAE--EFKKSAMYFILSQRYTITL
         ********..***** *.     ************  *  ***  ******.*.**

26695A   HQNPNESSDLVFSNPLGAARKILSYQNTKRVFYTGENESPNFNLFDYAIGFDELDFNDRY
26695B   HQNPNEFSDLVFSNPLGAARKILSYQNTKRVFYTGENESPNFNLFDYAIGFDELDFNDRY
1182     HQNPNEPSDLVFGSPIGSARKILSYQNAKRVFYTGENESPNFNLFDYAIGFDELDFRDRY
763      HQNPNEFSDLVFGNPLGSARKILSYQNAKRVFYTGENESPNFNLFDYAIGFDELDFNDRY
11637    HRNPDKPADIVFGNPLGSARKILSYQNTKRIFYTGENESPNFNLFDYAIGFDELDFRDRY
802      HQNPNEPSDLVFGSPIGAARKILSYQNTKRVFYAGENEVPNFNLFDYAIGFDELDLRDRY
         *.**     .*.**   *.*.**********.**.** ****.****************  ***

26695A   LRMPLYYAHLHYEAELVNDTTAPYKLKDNSLYALKKPSHHFKENHPNLCAVVNDESDLLK
26695B   LRMPLYYAHLHYKAELVNDTTAPYKLKDNSLYALKKPSHHFKENHPNLCAVVNDESDLLK
1182     LRMPLYYDRLHHKAESVNDTTSPYKLKPDSLYALKKPSHHFKENHPNLCAVVNNESDPLK
763      LRMPLYYDRLHHKAESVNDTTAPYKLKDNSLYALKKPSHCFKEKHPNLCAVVNDESDPLK
11637    LRMPLYYDRLHHKAESVNDTTAPYKIKGNSLYTLKKPSHCFKENHPNLCALINNESDPLK
802      LRMPLYYDRLHHKAESVNDTTAPYKIKPDSLYTLKKPSHHFKEKHPHLCAVVNDESDPLK
         ******* .**  ** ***** ***.*   *** ********* ** ***.*  * *** **

26695A   RGFASFVASNANAPMRNAFYDALNSIEPVTGGGSVRNTLGYKVGNKSEFLSQYKFNLCFE
26695B   RGFASFVASNANAPMRNAFYDALNSIEPVTGGGSVRNTLGYKVGNKSEFLSQYKFNLCFE
1182     RGFASFVASNPNAPKRNAFYDVLNSIEPVIGGGSVKNTLGYNIKNKSEFLSQYKFNLCFE
763      RGFASFVASNPNAPIRNAFYDALNSIEPVTGGGSVRNTLGYNVKNKNEFLSQYKFNLCFE
11637    RGFASFVASNANAPMRNAFYDALNSIEPVTGGGAVKNTLGYKVGNKSEFLSQYKFNLCFE
802      RGFASFVASNPNAPKRNAFYDALNSIEPVTGGGSVKNTLGYKVGNKNEFLSQYKFNLCFE
         **********  ***.******  *******  ***.*****  ** *************
```

FIG. 6A

```
26695A  NSQGYGYVTEKILDAYFSHTIPIYWGSPSVAKDFNPKSFVNVHDFNNFDEAIDYIKYLHT
26695B  NSQGYGYVTEKILDAYFSHTIPIYWGSPSVAKDFNPKSFVNVHDFNNFDEAIDYIKYLHT
1182    NSQGYGYVTEKIIDAYFSHTIPIYWGSPSVAQDFNPKSFVNVCDFKDFDEAIDHVRYLHT
763     NTQGYGYVTEKIIDAYFSHTIPIYWGSPSVAKDFNPKSFVNVHDFKNFDEAIDYIKYLHT
11637   NSQGYGYVTEKIIDAYFSHTIPIYWGSPSVAKDFNPKSFVNVHDFNNFDEAIDYVRYLHT
802     NSQGYGYVTEKIIDAYFSHTIPIYWGSPSVAKDFNPKSFVNVHDFKNFDEAIDYVRYLHT
        *.**********.*******************.********* ** ****** ..****

26695A  HPNAYLDMLYENPLNTLDGKAYFYQDLSFKKILDFFKTILENDTIYHN--NPFIFYRDLH
26695B  HPNAYLDMLYENPLNTLDGKAYFYQDLSFKKILDFFKTILENDTIYHKFSTSFMWEYDLH
1182    HPNAYLDMLYENPLNTLDGKAYFYQNLSFKKILDFFKTILENDTIYHD--NPFIFYRDLN
763     HKNAYLDMLYENPLNTLDGKAYFYQNLSFKKILAFFKTILENDTIYHD--NPFIFCRDLN
11637   HPNAYLDMLYENPLNTLDGKAYFYQNLSFKKILDFFKTILENDTIYHN--NPFIFYRDLN
802     HPNAYLDMLYENPLNTLDGKAYFYQDLSFKKILDFFKTILENDTIYHN--NPFVFYRDLN
        * ************************ ****** ************      *.  **.

26695A  EPLISI-------DDLRVNYDDLRVNYDDLRVNYDDLRVNYDDLRVNYDDLR
26695B  KPLVSI-----------------------------------------------
1182    EPLISIDDDLRVNYDDLRVNYDDLRVNYDDLRVNYDDLRVNYDDLRVNYDDLR
763     EPLVTI-------DDLRVNYDDLRVNYDDLRINYDDLRVNYDDLRINYDDLRVNYDDLR
11637   EPLVSI-----------------------DNLRINYDNLRVNYDDLRVNYDDLR
802     EPLVSI-----------------------------------DDLRADYNNLR
        **..*

26695A  VNYDDLRVNYDDLRVNYDRLLQNASPLLELSQNTTFKIYRKAYQKSLPLLRTI
26695B  ---------DDLRVNYDDLRVNYDRLLQNASPLLELSQNTTFKIYRKAYQKSLPLLRAV
1182    VNYDDLRVNYDDLRVNYDDLRVNYERLLQNASPLLELSQNTTFKIYRKAYQKSLPLLRAA
763     VNYDDLRINYDDLRVNYDDLRVNYERLLSKATPLLELSQNTTSKIYRKAYQKSLPLLRAI
11637   VNYDDLRINYDDLRINYDDLRINYERLLQNASPLLELSQNTSFKIYRKIYQKSLPLLRVI
802     ADYNNLRADYNNLRADYNNLRADYDRLLQNRSPLLELSQNTTFKIYHKAYHKSLPLLRAI
        ** * ** *.***  .********. ***.* *.*******

26695A  RRWVKK----
26695B  RKLVKKLGL-
1182    RKLIKKLGL-
763     RRWVKKLGL-
11637   RRWVKK----
802     RRWVKKLGL-
        *. .**
```

FIG. 6B

SEQUENCE LISTING

<160> NUMBER OF SEQ ID NOS: 27

<210> SEQ ID NO 1
<211> LENGTH: 464
<212> TYPE: PRT
<213> ORGANISM: Helicobacter pylori

<400> SEQUENCE: 1

```
Met Phe Gln Pro Leu Leu Asp Ala Tyr Val Glu Ser Ala Ser Ile Glu
 1               5                  10                  15

Lys Met Ala Ser Lys Ser Pro Pro Leu Lys Ile Ala Val Ala Asn
             20                  25                  30

Trp Trp Gly Asp Glu Glu Ile Lys Glu Phe Lys Asn Ser Val Leu Tyr
             35                  40                  45

Phe Ile Leu Ser Gln Arg Tyr Thr Ile Thr Leu His Gln Asn Pro Asn
     50                  55                  60

Glu Phe Ser Asp Leu Val Phe Gly Asn Pro Leu Gly Ser Ala Arg Lys
 65                  70                  75                  80

Ile Leu Ser Tyr Gln Asn Ala Lys Arg Val Phe Tyr Thr Gly Glu Asn
                 85                  90                  95

Glu Ser Pro Asn Phe Asn Leu Phe Asp Tyr Ala Ile Gly Phe Asp Glu
                100                 105                 110

Leu Asp Phe Asn Asp Arg Tyr Leu Arg Met Pro Leu Tyr Tyr Asp Arg
            115                 120                 125

Leu His His Lys Ala Glu Ser Val Asn Asp Thr Thr Ala Pro Tyr Lys
        130                 135                 140

Leu Lys Asp Asn Ser Leu Tyr Ala Leu Lys Lys Pro Ser His Cys Phe
145                 150                 155                 160

Lys Glu Lys His Pro Asn Leu Cys Ala Val Val Asn Asp Glu Ser Asp
                165                 170                 175

Pro Leu Lys Arg Gly Phe Ala Ser Phe Val Ala Ser Asn Pro Asn Ala
            180                 185                 190

Pro Ile Arg Asn Ala Phe Tyr Asp Ala Leu Asn Ser Ile Glu Pro Val
        195                 200                 205

Thr Gly Gly Gly Ser Val Arg Asn Thr Leu Gly Tyr Asn Val Lys Asn
```

-continued

```
                210                 215                 220
Lys Asn Glu Phe Leu Ser Gln Tyr Lys Phe Asn Leu Cys Phe Glu Asn
225                 230                 235                 240

Thr Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Lys Asp
                260                 265                 270

Phe Asn Pro Lys Ser Phe Val Asn Val His Asp Phe Lys Asn Phe Asp
            275                 280                 285

Glu Ala Ile Asp Tyr Ile Lys Tyr Leu His Thr His Lys Asn Ala Tyr
290                 295                 300

Leu Asp Met Leu Tyr Glu Asn Pro Leu Asn Thr Leu Asp Gly Lys Ala
305                 310                 315                 320

Tyr Phe Tyr Gln Asn Leu Ser Phe Lys Lys Ile Leu Ala Phe Phe Lys
                325                 330                 335

Thr Ile Leu Glu Asn Asp Thr Ile Tyr His Asp Asn Pro Phe Ile Phe
                340                 345                 350

Cys Arg Asp Leu Asn Glu Pro Leu Val Thr Ile Asp Asp Leu Arg Val
            355                 360                 365

Asn Tyr Asp Asp Leu Arg Val Asn Tyr Asp Asp Leu Arg Ile Asn Tyr
370                 375                 380

Asp Asp Leu Arg Val Asn Tyr Asp Asp Leu Arg Val Asn Tyr Asp Asp
385                 390                 395                 400

Leu Arg Ile Asn Tyr Asp Asp Leu Arg Val Asn Tyr Asp Asp Leu Arg
                405                 410                 415

Val Asn Tyr Glu Arg Leu Leu Ser Lys Ala Thr Pro Leu Leu Glu Leu
                420                 425                 430

Ser Gln Asn Thr Thr Ser Lys Ile Tyr Arg Lys Ala Tyr Gln Lys Ser
            435                 440                 445

Leu Pro Leu Leu Arg Ala Ile Arg Arg Trp Val Lys Lys Leu Gly Leu
450                 455                 460

<210> SEQ ID NO 2
<211> LENGTH: 486
<212> TYPE: PRT
<213> ORGANISM: Helicobacter pylori

<400> SEQUENCE: 2

Met Phe Gln Pro Leu Leu Asp Ala Tyr Ile Glu Ser Ala Ser Ile Glu
1               5                   10                  15

Lys Ile Thr Ser Lys Ser Pro Pro Leu Lys Ile Ala Val Ala Asn
            20                  25                  30

Trp Trp Gly Asp Glu Glu Val Glu Glu Phe Lys Lys Asn Ile Leu Tyr
        35                  40                  45

Phe Ile Leu Ser Gln His Tyr Thr Ile Thr Leu His Gln Asn Pro Asn
50                  55                  60

Glu Pro Ser Asp Leu Val Phe Gly Ser Pro Ile Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
            100                 105                 110

Leu Asp Phe Arg Asp Arg Tyr Leu Arg Met Pro Leu Tyr Tyr Asp Arg
            115                 120                 125
```

-continued

```
Leu His His Lys Ala Glu Ser Val Asn Asp Thr Thr Ser Pro Tyr Lys
    130                 135                 140

Leu Lys Pro Asp Ser Leu Tyr Ala Leu Lys Lys Pro Ser His His Phe
145                 150                 155                 160

Lys Glu Asn His Pro Asn Leu Cys Ala Val Val Asn Asn Glu Ser Asp
                165                 170                 175

Pro Leu Lys Arg Gly Phe Ala Ser Phe Val Ala Ser Asn Pro Asn Ala
            180                 185                 190

Pro Lys Arg Asn Ala Phe Tyr Asp Val Leu Asn Ser Ile Glu Pro Val
        195                 200                 205

Ile Gly Gly Gly Ser Val Lys Asn Thr Leu Gly Tyr Asn Ile Lys Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Gln Asp
            260                 265                 270

Phe Asn Pro Lys Ser Phe Val Asn Val Cys Asp Phe Lys Asp Phe Asp
        275                 280                 285

Glu Ala Ile Asp His Val Arg Tyr Leu His Thr His Pro Asn Ala Tyr
    290                 295                 300

Leu Asp Met Leu Tyr Glu Asn Pro Leu Asn Thr Leu Asp Gly Lys Ala
305                 310                 315                 320

Tyr Phe Tyr Gln Asn Leu Ser Phe Lys Lys Ile Leu Asp Phe Phe Lys
                325                 330                 335

Thr Ile Leu Glu Asn Asp Thr Ile Tyr His Asp Asn Pro Phe Ile Phe
            340                 345                 350

Tyr Arg Asp Leu Asn Glu Pro Leu Ile Ser Ile Asp Asp Leu Arg
        355                 360                 365

Val Asn Tyr Asp Asp Leu Arg Val Asn Tyr Asp Asp Leu Arg Val Asn
    370                 375                 380

Tyr Asp Asp Leu Arg Val Asn Tyr Asp Asp Leu Arg Val Asn Tyr Asp
385                 390                 395                 400

Asp Leu Arg Val Asn Tyr Asp Asp Leu Arg Val Asn Tyr Asp Asp Leu
                405                 410                 415

Arg Val Asn Tyr Asp Asp Leu Arg Val Asn Tyr Asp Asp Leu Arg Val
            420                 425                 430

Asn Tyr Asp Asp Leu Arg Val Asn Tyr Glu Arg Leu Leu Gln Asn Ala
        435                 440                 445

Ser Pro Leu Leu Glu Leu Ser Gln Asn Thr Thr Phe Lys Ile Tyr Arg
    450                 455                 460

Lys Ala Tyr Gln Lys Ser Leu Pro Leu Leu Arg Ala Ala Arg Lys Leu
465                 470                 475                 480

Ile Lys Lys Leu Gly Leu
                485
```

<210> SEQ ID NO 3
<211> LENGTH: 440
<212> TYPE: PRT
<213> ORGANISM: Helicobacter pylori

<400> SEQUENCE: 3

```
Met Phe Gln Pro Leu Leu Asp Ala Phe Ile Glu Ser Ala Ser Ile Lys
1               5                   10                  15
```

-continued

```
Lys Met Pro Leu Ser Tyr Pro Pro Leu Lys Ile Ala Val Ala Asn Trp
         20                  25                  30

Trp Gly Gly Ala Glu Glu Phe Lys Lys Ser Ala Met Tyr Phe Ile Leu
         35                  40                  45

Ser Gln Arg Tyr Thr Ile Thr Leu His Gln Asn Pro Asn Glu Pro Ser
         50                  55                  60

Asp Leu Val Phe Gly Ser Pro Ile Gly Ala Ala Arg Lys Ile Leu Ser
 65                  70                  75                  80

Tyr Gln Asn Thr Lys Arg Val Phe Tyr Ala Gly Glu Asn Glu Val Pro
                 85                  90                  95

Asn Phe Asn Leu Phe Asp Tyr Ala Ile Gly Phe Asp Glu Leu Asp Leu
                 100                 105                 110

Arg Asp Arg Tyr Leu Arg Met Pro Leu Tyr Tyr Asp Arg Leu His His
                 115                 120                 125

Lys Ala Glu Ser Val Asn Asp Thr Thr Ala Pro Tyr Lys Ile Lys Pro
         130                 135                 140

Asp Ser Leu Tyr Thr Leu Lys Lys Pro Ser His His Phe Lys Glu Lys
145                 150                 155                 160

His Pro His Leu Cys Ala Val Val Asn Asp Glu Ser Asp Pro Leu Lys
                 165                 170                 175

Arg Gly Phe Ala Ser Phe Val Ala Ser Asn Pro Asn Ala Pro Lys Arg
                 180                 185                 190

Asn Ala Phe Tyr Asp Ala Leu Asn Ser Ile Glu Pro Val Thr Gly Gly
                 195                 200                 205

Gly Ser Val Lys Asn Thr Leu Gly Tyr Lys Val Gly Asn Lys Asn Glu
         210                 215                 220

Phe Leu Ser Gln Tyr Lys Phe Asn Leu Cys Phe Glu Asn Ser Gln Gly
225                 230                 235                 240

Tyr Gly Tyr Val Thr Glu Lys Ile Ile Asp Ala Tyr Phe Ser His Thr
                 245                 250                 255

Ile Pro Ile Tyr Trp Gly Ser Pro Ser Val Ala Lys Asp Phe Asn Pro
                 260                 265                 270

Lys Ser Phe Val Asn Val His Asp Phe Lys Asn Phe Asp Glu Ala Ile
                 275                 280                 285

Asp Tyr Val Arg Tyr Leu His Thr His Pro Asn Ala Tyr Leu Asp Met
         290                 295                 300

Leu Tyr Glu Asn Pro Leu Asn Thr Leu Asp Gly Lys Ala Tyr Phe Tyr
305                 310                 315                 320

Gln Asp Leu Ser Phe Lys Lys Ile Leu Asp Phe Phe Lys Thr Ile Leu
                 325                 330                 335

Glu Asn Asp Thr Ile Tyr His Asn Asn Pro Phe Val Phe Tyr Arg Asp
                 340                 345                 350

Leu Asn Glu Pro Leu Val Ser Ile Asp Asp Leu Arg Ala Asp Tyr Asn
         355                 360                 365

Asn Leu Arg Ala Asp Tyr Asn Asn Leu Arg Ala Asp Tyr Asn Asn Leu
         370                 375                 380

Arg Ala Asp Tyr Asn Asn Leu Arg Ala Asp Tyr Asp Arg Leu Leu Gln
385                 390                 395                 400

Asn Arg Ser Pro Leu Leu Glu Leu Ser Gln Asn Thr Thr Phe Lys Ile
                 405                 410                 415

Tyr His Lys Ala Tyr His Lys Ser Leu Pro Leu Leu Arg Ala Ile Arg
         420                 425                 430
```

```
Arg Trp Val Lys Lys Leu Gly Leu
        435             440

<210> SEQ ID NO 4
<211> LENGTH: 1670
<212> TYPE: DNA
<213> ORGANISM: Helicobacter pylori
<220> FEATURE:
<221> NAME/KEY: CDS
<222> LOCATION: (145)...(1536)

<400> SEQUENCE: 4
tctggcttgc acagctatgc cgcaggcgat cccttgccga tccctacttt cttatacttt      60
ttggtagcga tacctttgc tcttgtgatc ttggcgtatt ttaaacgcca tttgagtttg     120
cctaaattgg tttaaaggat aacc atg ttc caa ccc cta tta gac gct tat       171
                           Met Phe Gln Pro Leu Leu Asp Ala Tyr
                             1               5 gta gaa agc gct tcc att gaa aaa atg gcc tct aaa tct ccc ccc ccc      219
Val Glu Ser Ala Ser Ile Glu Lys Met Ala Ser Lys Ser Pro Pro Pro
 10              15                  20                  25 cta aaa atc gct gtg gcg aat tgg tgg gga gat gaa gaa att aaa gaa      267
Leu Lys Ile Ala Val Ala Asn Trp Trp Gly Asp Glu Glu Ile Lys Glu
             30                  35                  40 ttt aaa aat agc gtt ctt tat ttt atc cta agc caa cgc tac aca atc      315
Phe Lys Asn Ser Val Leu Tyr Phe Ile Leu Ser Gln Arg Tyr Thr Ile
         45                  50                  55 acc ctc cac caa aac ccc aat gaa ttt tca gat ctc gtc ttt ggt aac      363
Thr Leu His Gln Asn Pro Asn Glu Phe Ser Asp Leu Val Phe Gly Asn
     60                  65                  70 ccc ctt gga tcg gcc aga aaa atc tta tcc tat caa aac gct aaa cga      411
Pro Leu Gly Ser Ala Arg Lys Ile Leu Ser Tyr Gln Asn Ala Lys Arg
 75                  80                  85 gtg ttt tac acc ggt gaa aac gaa tcg cct aat ttc aac ctc ttt gat      459
Val Phe Tyr Thr Gly Glu Asn Glu Ser Pro Asn Phe Asn Leu Phe Asp
 90                  95                 100                 105 tac gcc ata ggc ttt gat gaa ttg gat ttt aat gat cgt tat ttg aga      507
Tyr Ala Ile Gly Phe Asp Glu Leu Asp Phe Asn Asp Arg Tyr Leu Arg
                 110                 115                 120 atg cct tta tat tat gat agg cta cac cat aaa gcc gag agc gtg aat      555
Met Pro Leu Tyr Tyr Asp Arg Leu His His Lys Ala Glu Ser Val Asn
             125                 130                 135 gac acc act gcg ccc tac aaa ctc aaa gat aac agc ctt tat gct tta      603
Asp Thr Thr Ala Pro Tyr Lys Leu Lys Asp Asn Ser Leu Tyr Ala Leu
         140                 145                 150 aaa aaa ccc tcc cat tgt ttt aaa gaa aaa cac ccc aat tta tgc gca      651
Lys Lys Pro Ser His Cys Phe Lys Glu Lys His Pro Asn Leu Cys Ala
     155                 160                 165 gta gtg aat gat gag agc gat cct ttg aaa aga ggg ttt gcg agc ttt      699
Val Val Asn Asp Glu Ser Asp Pro Leu Lys Arg Gly Phe Ala Ser Phe
170                 175                 180                 185 gtc gcg agc aac cct aac gcc cct ata agg aac gct ttc tat gac gct      747
Val Ala Ser Asn Pro Asn Ala Pro Ile Arg Asn Ala Phe Tyr Asp Ala
                 190                 195                 200 cta aat tct att gaa cca gtt act ggg gga ggg agc gtg aga aac act      795
Leu Asn Ser Ile Glu Pro Val Thr Gly Gly Gly Ser Val Arg Asn Thr
             205                 210                 215 tta ggc tat aac gtc aaa aac aaa aac gag ttt tta agc caa tac aag      843
Leu Gly Tyr Asn Val Lys Asn Lys Asn Glu Phe Leu Ser Gln Tyr Lys
         220                 225                 230 ttc aac ctg tgt ttt gaa aac act caa ggc tat ggc tat gta act gaa      891
```

```
Phe Asn Leu Cys Phe Glu Asn Thr Gln Gly Tyr Gly Tyr Val Thr Glu
    235                 240                 245 aaa atc att gac gct tac ttt agc cat acc att cct att tat tgg ggg       939
Lys Ile Ile Asp Ala Tyr Phe Ser His Thr Ile Pro Ile Tyr Trp Gly
250                 255                 260                 265 agt cct agc gtg gcg aaa gat ttt aac cct aaa agt ttt gtg aat gtg       987
Ser Pro Ser Val Ala Lys Asp Phe Asn Pro Lys Ser Phe Val Asn Val
                270                 275                 280 cat gat ttc aaa aac ttt gat gaa gcg att gac tat atc aaa tac ttg      1035
His Asp Phe Lys Asn Phe Asp Glu Ala Ile Asp Tyr Ile Lys Tyr Leu
            285                 290                 295 cac acg cac aaa aac gct tat tta gac atg ctt tat gaa aac cct ttg      1083
His Thr His Lys Asn Ala Tyr Leu Asp Met Leu Tyr Glu Asn Pro Leu
        300                 305                 310 aac acc ctt gat ggg aaa gct tac ttt tac caa aat ttg agt ttt aaa      1131
Asn Thr Leu Asp Gly Lys Ala Tyr Phe Tyr Gln Asn Leu Ser Phe Lys
    315                 320                 325 aag atc cta gct ttt ttt aaa acg att tta gaa aac gat acg att tat      1179
Lys Ile Leu Ala Phe Phe Lys Thr Ile Leu Glu Asn Asp Thr Ile Tyr
330                 335                 340                 345 cac gat aac cct ttc att ttc tgt cgt gat ttg aat gag cct tta gta      1227
His Asp Asn Pro Phe Ile Phe Cys Arg Asp Leu Asn Glu Pro Leu Val
                350                 355                 360 act att gat gat ttg agg gtt aat tat gat gat ttg agg gtt aat tat      1275
Thr Ile Asp Asp Leu Arg Val Asn Tyr Asp Asp Leu Arg Val Asn Tyr
            365                 370                 375 gat gat ttg aga att aat tat gat gat ttg agg gtt aat tat gat gat      1323
Asp Asp Leu Arg Ile Asn Tyr Asp Asp Leu Arg Val Asn Tyr Asp Asp
        380                 385                 390 ttg agg gtt aat tat gat gat ttg aga att aat tat gat gat ttg agg      1371
Leu Arg Val Asn Tyr Asp Asp Leu Arg Ile Asn Tyr Asp Asp Leu Arg
    395                 400                 405 gtt aat tat gat gat ttg agg gtt aat tat gag cgc ctc tta tca aaa      1419
Val Asn Tyr Asp Asp Leu Arg Val Asn Tyr Glu Arg Leu Leu Ser Lys
410                 415                 420                 425 gct acc cct ctt ttg gaa tta tcc caa aac acc act tct aaa atc tat      1467
Ala Thr Pro Leu Leu Glu Leu Ser Gln Asn Thr Thr Ser Lys Ile Tyr
                430                 435                 440 cgc aaa gct tac caa aaa tcc tta cct ttg ttg cgc gcc ata agg aga      1515
Arg Lys Ala Tyr Gln Lys Ser Leu Pro Leu Leu Arg Ala Ile Arg Arg
            445                 450                 455 tgg gtt aaa aaa ttg ggt ttg taaaattggg gtaaactaa accccttgcg          1566
Trp Val Lys Lys Leu Gly Leu
        460 ctatcatcgc agacgctact tttctaaaac cagcgatatt agcccctaaa acaaaattat    1626 gagggtcttt aaactcttta gcggtttgag agacattctt ataa                    1670

<210> SEQ ID NO 5
<211> LENGTH: 476
<212> TYPE: PRT
<213> ORGANISM: Helicobacter pylori

<400> SEQUENCE: 5

Met Phe Gln Pro Leu Leu Asp Ala Phe Ile Glu Ser Ala Ser Ile Glu
1               5                   10                  15

Lys Met Val Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45
```

```
Tyr Phe Ile Leu Ser Gln Arg Tyr Ala Ile Thr Leu His Gln Asn Pro
 50                  55                  60

Asn Glu Ser Ser Asp Leu Val Phe Ser Asn Pro Leu Gly Ala Ala Arg
 65                  70                  75                  80

Lys Ile Leu Ser Tyr Gln Asn Thr Lys Arg Val Phe Tyr Thr Gly Glu
                 85                  90                  95

Asn Glu Ser Pro Asn Phe Asn Leu Phe Asp Tyr Ala Ile Gly Phe Asp
                100                 105                 110

Glu Leu Asp Phe Asn Asp Arg Tyr Leu Arg Met Pro Leu Tyr Tyr Ala
             115                 120                 125

His Leu His Tyr Glu Ala Glu Leu Val Asn Asp Thr Thr Ala Pro Tyr
     130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
             180                 185                 190

Ala Pro Met Arg Asn Ala Phe Tyr Asp Ala Leu Asn Ser Ile Glu Pro
         195                 200                 205

Val Thr Gly Gly Gly Ser Val Arg Asn Thr Leu Gly Tyr Lys Val Gly
     210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
             260                 265                 270

Asp Phe Asn Pro Lys Ser Phe Val Asn Val His Asp Phe Asn Asn Phe
         275                 280                 285

Asp Glu Ala Ile Asp Tyr Ile Lys Tyr Leu His Thr His Pro Asn Ala
     290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Asn Asn Pro Phe Ile
             340                 345                 350

Phe Tyr Arg Asp Leu His Glu Pro Leu Ile Ser Ile Asp Asp Leu Arg
         355                 360                 365

Val Asn Tyr Asp Asp Leu Arg Val Asn Tyr Asp Asp Leu Arg Val Asn
     370                 375                 380

Tyr Asp Asp Leu Arg Val Asn Tyr Asp Asp Leu Arg Val Asn Tyr Asp
385                 390                 395                 400

Asp Leu Arg Val Asn Tyr Asp Asp Leu Arg Val Asn Tyr Asp Asp Leu
                405                 410                 415

Arg Val Asn Tyr Asp Asp Leu Arg Val Asn Tyr Asp Asp Leu Arg Val
             420                 425                 430

Asn Tyr Asp Arg Leu Leu Gln Asn Ala Ser Pro Leu Leu Glu Leu Ser
         435                 440                 445

Gln Asn Thr Thr Phe Lys Ile Tyr Arg Lys Ala Tyr Gln Lys Ser Leu
     450                 455                 460
```

```
Pro Leu Leu Arg Thr Ile Arg Arg Trp Val Lys Lys
465                 470                 475
```

<210> SEQ ID NO 6
<211> LENGTH: 425
<212> TYPE: PRT
<213> ORGANISM: Helicobacter pylori

<400> SEQUENCE: 6

```
Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
            35                  40                  45

Tyr Phe Ile Leu Ser Gln Arg Tyr Ala Ile Thr Leu His Gln Asn Pro
50                  55                  60

Asn Glu Phe Ser Asp Leu Val Phe Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
            115                 120                 125

His Leu His Tyr Lys Ala Glu Leu Val Asn Asp Thr Thr Ala Pro Tyr
            130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
            195                 200                 205

Val Thr Gly Gly Gly Ser Val Arg Asn Thr Leu Gly Tyr Lys Val Gly
210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
            275                 280                 285

Asp Glu Ala Ile Asp Tyr Ile Lys Tyr Leu His Thr His Pro Asn Ala
290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp
            355                 360                 365
```

```
Leu Arg Val Asn Tyr Asp Asp Leu Arg Val Asn Tyr Asp Arg Leu Leu
    370                 375                 380

Gln Asn Ala Ser Pro Leu Leu Glu Leu Ser Gln Asn Thr Thr Phe Lys
385                 390                 395                 400

Ile Tyr Arg Lys Ala Tyr Gln Lys Ser Leu Pro Leu Leu Arg Ala Val
                405                 410                 415

Arg Lys Leu Val Lys Lys Leu Gly Leu
                420                 425

<210> SEQ ID NO 7
<211> LENGTH: 478
<212> TYPE: PRT
<213> ORGANISM: Helicobacter pylori

<400> SEQUENCE: 7

Met Phe Gln Pro Leu Leu Asp Ala Tyr Val Glu Ser Ala Ser Ile Glu
1               5                   10                  15

Lys Met Ala Ser Lys Ser Pro Pro Leu Lys Ile Ala Val Ala Asn
            20                  25                  30

Trp Trp Gly Asp Glu Glu Ile Lys Glu Phe Lys Asn Ser Val Leu Tyr
            35                  40                  45

Phe Ile Leu Ser Gln Arg Tyr Thr Ile Thr Leu His Gln Asn Pro Asn
    50                  55                  60

Glu Phe Ser Asp Leu Val Phe Gly Asn Pro Leu Gly Ser Ala Arg Lys
65                  70                  75                  80

Ile Leu Ser Tyr Gln Asn Ala Lys Arg Val Phe Tyr Thr Gly Glu Asn
                85                  90                  95

Glu Ser Pro Asn Phe Asn Leu Phe Asp Tyr Ala Ile Gly Phe Asp Glu
                100                 105                 110

Leu Asp Phe Asn Asp Arg Tyr Leu Arg Met Pro Leu Tyr Tyr Asp Arg
                115                 120                 125

Leu His His Lys Ala Glu Ser Val Asn Asp Thr Thr Ala Pro Tyr Lys
    130                 135                 140

Leu Lys Asp Asn Ser Leu Tyr Ala Leu Lys Lys Pro Ser His Cys Phe
145                 150                 155                 160

Lys Glu Lys His Pro Asn Leu Cys Ala Val Val Asn Asp Glu Ser Asp
                165                 170                 175

Pro Leu Lys Arg Gly Phe Ala Ser Phe Val Ala Ser Asn Pro Asn Ala
                180                 185                 190

Pro Ile Arg Asn Ala Phe Tyr Asp Ala Leu Asn Ser Ile Glu Pro Val
                195                 200                 205

Thr Gly Gly Gly Ser Val Arg Asn Thr Leu Gly Tyr Asn Val Lys Asn
    210                 215                 220

Lys Asn Glu Phe Leu Ser Gln Tyr Lys Phe Asn Leu Cys Phe Glu Asn
225                 230                 235                 240

Thr Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Lys Asp
                260                 265                 270

Phe Asn Pro Lys Ser Phe Val Asn Val His Asp Phe Lys Asn Phe Asp
                275                 280                 285

Glu Ala Ile Asp Tyr Ile Lys Tyr Leu His Thr His Lys Asn Ala Tyr
                290                 295                 300

Leu Asp Met Leu Tyr Glu Asn Pro Leu Asn Thr Leu Asp Gly Lys Ala
```

```
305                     310                     315                     320
Tyr Phe Tyr Gln Asn Leu Ser Phe Lys Lys Ile Leu Ala Phe Phe Lys
                325                     330                     335

Thr Ile Leu Glu Asn Asp Thr Ile Tyr His Asp Asn Pro Phe Ile Phe
                340                     345                     350

Cys Arg Asp Leu Asn Glu Pro Leu Val Thr Ile Asp Asp Leu Arg Val
                355                     360                     365

Asn Tyr Asp Asp Leu Arg Val Asn Tyr Asp Asp Leu Arg Ile Asn Tyr
                370                     375                     380

Asp Asp Leu Arg Val Asn Tyr Asp Asp Leu Arg Ile Asn Tyr Asp Asp
385                     390                     395                     400

Leu Arg Val Asn Tyr Asp Asp Leu Arg Val Asn Tyr Asp Asp Leu Arg
                405                     410                     415

Ile Asn Tyr Asp Asp Leu Arg Val Asn Tyr Asp Asp Leu Arg Val Asn
                420                     425                     430

Tyr Glu Arg Leu Leu Ser Lys Ala Thr Pro Leu Leu Glu Leu Ser Gln
                435                     440                     445

Asn Thr Thr Ser Lys Ile Tyr Arg Lys Ala Tyr Gln Lys Ser Leu Pro
    450                     455                     460

Leu Leu Arg Ala Ile Arg Arg Trp Val Lys Lys Leu Gly Leu
465                     470                     475
```

<210> SEQ ID NO 8
<211> LENGTH: 454
<212> TYPE: PRT
<213> ORGANISM: Helicobacter pylori

<400> SEQUENCE: 8

```
Met Phe Gln Pro Leu Leu Asp Ala Phe Ile Glu Ser Ala Ser Ile Glu
1               5                   10                  15

Lys Met Ala Ser Lys Ser Pro Pro Leu Lys Ile Ala Val Ala Asn
                20                  25                  30

Trp Trp Gly Asp Glu Glu Ile Lys Glu Phe Lys Lys Ser Thr Leu Tyr
            35                      40                  45

Phe Ile Leu Ser Gln His Tyr Thr Ile Thr Leu His Arg Asn Pro Asp
    50                      55                  60

Lys Pro Ala Asp Ile Val Phe Gly Asn Pro Leu Gly Ser Ala Arg Lys
65                  70                  75                      80

Ile Leu Ser Tyr Gln Asn Thr Lys Arg Ile Phe Tyr Thr Gly Glu Asn
                85                      90                  95

Glu Ser Pro Asn Phe Asn Leu Phe Asp Tyr Ala Ile Gly Phe Asp Glu
            100                     105                 110

Leu Asp Phe Arg Asp Arg Tyr Leu Arg Met Pro Leu Tyr Tyr Asp Arg
            115                     120                 125

Leu His His Lys Ala Glu Ser Val Asn Asp Thr Thr Ala Pro Tyr Lys
    130                     135                 140

Ile Lys Gly Asn Ser Leu Tyr Thr Leu Lys Lys Pro Ser His Cys Phe
145                 150                 155                 160

Lys Glu Asn His Pro Asn Leu Cys Ala Leu Ile Asn Asn Glu Ser Asp
                165                     170                 175

Pro Leu Lys Arg Gly Phe Ala Ser Phe Val Ala Ser Asn Ala Asn Ala
            180                     185                 190

Pro Met Arg Asn Ala Phe Tyr Asp Ala Leu Asn Ser Ile Glu Pro Val
            195                     200                 205
```

```
Thr Gly Gly Gly Ala Val Lys Asn Thr Leu Gly Tyr Lys Val Gly Asn
    210                 215                 220

Lys Ser Glu Phe Leu Ser Gln Tyr Lys Phe Asn Leu Cys Phe Glu Asn
225                 230                 235                 240

Ser Gln Gly Tyr Gly Tyr Val Thr Glu Lys Ile Ile Asp Ala Tyr Phe
                245                 250                 255

Ser His Thr Ile Pro Ile Tyr Trp Gly Ser Pro Ser Val Ala Lys Asp
            260                 265                 270

Phe Asn Pro Lys Ser Phe Val Asn Val His Asp Phe Asn Asn Phe Asp
        275                 280                 285

Glu Ala Ile Asp Tyr Val Arg Tyr Leu His Thr His Pro Asn Ala Tyr
    290                 295                 300

Leu Asp Met Leu Tyr Glu Asn Pro Leu Asn Thr Leu Asp Gly Lys Ala
305                 310                 315                 320

Tyr Phe Tyr Gln Asn Leu Ser Phe Lys Lys Ile Leu Asp Phe Phe Lys
                325                 330                 335

Thr Ile Leu Glu Asn Asp Thr Ile Tyr His Asn Asn Pro Phe Ile Phe
            340                 345                 350

Tyr Arg Asp Leu Asn Glu Pro Leu Val Ser Ile Asp Asn Leu Arg Ile
        355                 360                 365

Asn Tyr Asp Asn Leu Arg Val Asn Tyr Asp Asp Leu Arg Val Asn Tyr
370                 375                 380

Asp Asp Leu Arg Val Asn Tyr Asp Asp Leu Arg Ile Asn Tyr Asp Asp
385                 390                 395                 400

Leu Arg Ile Asn Tyr Asp Asp Leu Arg Ile Asn Tyr Glu Arg Leu Leu
                405                 410                 415

Gln Asn Ala Ser Pro Leu Leu Glu Leu Ser Gln Asn Thr Ser Phe Lys
            420                 425                 430

Ile Tyr Arg Lys Ile Tyr Gln Lys Ser Leu Pro Leu Leu Arg Val Ile
        435                 440                 445

Arg Arg Trp Val Lys Lys
    450

<210> SEQ ID NO 9
<211> LENGTH: 365
<212> TYPE: PRT
<213> ORGANISM: Bos taurus

<400> SEQUENCE: 9

Met Tyr Pro Pro Gly Cys Ala Lys Val Lys Cys Ser Trp His His Cys
1               5                   10                  15

Leu Pro Gly Leu Leu Gln Leu Leu Leu Ala Leu Cys Phe Phe Ser
            20                  25                  30

Tyr Leu Arg Met Ser Gln Glu Lys Pro Lys Pro Lys Pro Met Trp Val
            35                  40                  45

Ser Glu Leu Gly Ala Pro Ser Gln Ala Thr Glu Gly Ser Ser Ala His
50                  55                  60

Leu Pro Leu Arg Val Leu Leu Trp Thr Trp Pro Phe Asn Gln Pro Val
65                  70                  75                  80

Ala Leu Ser Arg Cys Ser Glu Leu Trp Pro Gly Thr Ala Asp Cys Gln
                85                  90                  95

Leu Thr Val Asn Arg Ser Glu Tyr Pro Gln Ala Asp Ala Val Phe Val
            100                 105                 110

His His Arg Glu Val Ser His Arg Pro Lys Met Gln Leu Pro Pro Ser
        115                 120                 125
```

-continued

Pro Arg Pro Ala Asp Gln Arg Trp Val Trp Phe Ser Met Glu Ser Pro
    130                 135                 140

Ser Asn Cys Leu Lys Leu Lys Asp Leu Asp Gly Tyr Phe Asn Leu Thr
145                 150                 155                 160

Met Ser Thr Arg Arg Asp Ser Asp Ile Phe Met Pro Tyr Gly Trp Leu
            165                 170                 175

Glu Pro Trp Pro Ser Gln Pro Val Glu Thr Leu Leu Asn Ile Ser Ala
            180                 185                 190

Lys Thr Lys Leu Val Ala Trp Val Ser Asn Trp Asn Thr Asp Ser
        195                 200                 205

Ile Arg Val Gln Tyr Tyr Lys Leu Leu Lys Pro His Leu Gln Val Asp
    210                 215                 220

Val Tyr Gly Arg Phe His Thr Pro Leu Pro His Ala Leu Met Ala Lys
225                 230                 235                 240

Gln Leu Ser Gln Tyr Lys Phe Tyr Leu Ala Phe Glu Asn Ser Leu His
                245                 250                 255

Pro Asp Tyr Ile Thr Glu Lys Leu Trp Lys Asn Ala Leu Gln Ala Trp
            260                 265                 270

Ala Val Pro Val Val Leu Gly Pro Ser Arg Val Asn Tyr Glu Gln Phe
        275                 280                 285

Leu Pro Pro Lys Ala Phe Ile His Val Glu Asp Phe Gln Ser Pro Lys
    290                 295                 300

Asp Leu Ala Gln Tyr Leu Leu Ala Leu Asp Lys Asp Tyr Ala Ser Tyr
305                 310                 315                 320

Leu Asn Tyr Phe Arg Trp Arg Glu Thr Leu Arg Pro Arg Ser Phe Ser
                325                 330                 335

Trp Ala Leu Met Phe Cys Lys Ala Cys Trp Lys Leu Gln Gln Glu Pro
            340                 345                 350

Arg Tyr Gln Thr Val Pro Ser Ile Ala Ser Trp Phe Gln
        355                 360                 365

<210> SEQ ID NO 10
<211> LENGTH: 359
<212> TYPE: PRT
<213> ORGANISM: Homo sapiens

<400> SEQUENCE: 10

Met Asp Pro Leu Gly Pro Ala Lys Pro Gln Trp Ser Trp Arg Cys Cys
1               5                   10                  15

Leu Thr Thr Leu Leu Phe Gln Leu Leu Met Ala Val Cys Phe Phe Ser
            20                  25                  30

Tyr Leu Arg Val Ser Gln Asp Asp Pro Thr Val Tyr Pro Asn Gly Ser
        35                  40                  45

Arg Phe Pro Asp Ser Thr Gly Thr Pro Ala His Ser Ile Pro Leu Ile
    50                  55                  60

Leu Leu Trp Thr Trp Pro Phe Asn Lys Pro Ile Ala Leu Pro Arg Cys
65                  70                  75                  80

Ser Glu Met Val Pro Gly Thr Ala Asp Cys Asn Ile Thr Ala Asp Arg
                85                  90                  95

Lys Val Tyr Pro Gln Ala Asp Ala Val Ile Val His His Arg Glu Val
            100                 105                 110

Met Tyr Asn Pro Ser Ala Gln Leu Pro Arg Ser Pro Arg Arg Gln Gly
        115                 120                 125

Gln Arg Trp Ile Trp Phe Ser Met Glu Ser Pro Ser His Cys Trp Gln

-continued

```
            130                 135                 140
Leu Lys Ala Met Asp Gly Tyr Phe Asn Leu Thr Met Ser Tyr Arg Ser
145                 150                 155                 160
Asp Ser Asp Ile Phe Thr Pro Tyr Gly Trp Leu Glu Pro Trp Ser Gly
                165                 170                 175
Gln Pro Ala His Pro Pro Leu Asn Leu Ser Ala Lys Thr Glu Leu Val
            180                 185                 190
Ala Trp Ala Val Ser Asn Trp Gly Pro Asn Ser Ala Arg Val Arg Tyr
        195                 200                 205
Tyr Gln Ser Leu Gln Ala His Leu Lys Val Asp Val Tyr Gly Arg Ser
    210                 215                 220
His Lys Pro Leu Pro Gln Gly Thr Met Met Glu Thr Leu Ser Arg Tyr
225                 230                 235                 240
Lys Phe Tyr Leu Ala Phe Glu Asn Ser Leu His Pro Asp Tyr Ile Thr
                245                 250                 255
Glu Lys Leu Trp Arg Asn Ala Leu Glu Ala Trp Ala Val Pro Val Val
            260                 265                 270
Leu Gly Pro Ser Arg Ser Asn Tyr Glu Arg Phe Leu Pro Pro Asp Ala
        275                 280                 285
Phe Ile His Val Asp Asp Phe Gln Ser Pro Lys Asp Leu Ala Arg Tyr
    290                 295                 300
Leu Gln Glu Leu Asp Lys Asp His Ala Arg Tyr Leu Ser Tyr Phe Arg
305                 310                 315                 320
Trp Arg Glu Thr Leu Arg Pro Arg Ser Phe Ser Trp Ala Leu Ala Phe
                325                 330                 335
Cys Lys Ala Cys Trp Lys Leu Gln Glu Glu Ser Arg Tyr Gln Thr Arg
            340                 345                 350
Gly Ile Ala Ala Trp Phe Thr
        355

<210> SEQ ID NO 11
<211> LENGTH: 433
<212> TYPE: PRT
<213> ORGANISM: Mus musculus

<400> SEQUENCE: 11

Met Ala Pro Ala Arg Gln Glu Leu Gln His Glu Ser Arg Cys Arg Pro
1               5                   10                  15
Ser Arg Thr Val Asp Ala Trp Arg Ala Val Ala Thr Arg Gly Arg
            20                  25                  30
His Met Glu Thr Pro Gly Tyr Arg Arg Arg Thr Arg Cys Gly Gly Trp
        35                  40                  45
Gly Leu Pro Arg Ser Val Ser Ser Leu Ala Ala Val Gly Leu Leu Cys
    50                  55                  60
Thr Ala Leu Thr Thr Phe Ile Cys Trp Gly Gln Leu Pro Pro Leu Pro
65                  70                  75                  80
Trp Ala Ser Pro Ala Pro Gln Arg Leu Val Gly Val Leu Leu Trp Trp
                85                  90                  95
Glu Pro Phe Arg Gly Arg Gly Tyr Pro Lys Ser Pro Pro Asp Cys
            100                 105                 110
Ser Leu Arg Phe Asn Ile Ser Gly Cys Arg Leu Leu Thr Asp Arg Ala
        115                 120                 125
Ala Tyr Gly Glu Ala Gln Ala Val Leu Phe His His Arg Asp Leu Val
    130                 135                 140
```

-continued

Lys Glu Leu His Asp Trp Pro Pro Trp Gly Ala Arg Glu Arg Thr
145                 150                 155                 160

Asp Lys Ala Leu Val Leu Arg Val Phe Asp Gln Glu Gly Ala Val
                165                 170                 175

Thr Leu Thr Gly Lys Ala Leu Glu Thr Val Gly Ser Arg Pro Pro Gly
            180                 185                 190

Gln Arg Trp Val Trp Met Asn Phe Glu Ser Pro Ser His Thr Pro Gly
                195                 200                 205

Leu Arg Gly Leu Ala Lys Asp Leu Phe Asn Trp Thr Leu Ser Tyr Arg
            210                 215                 220

Thr Asp Ser Asp Val Phe Val Pro Tyr Gly Phe Leu Tyr Ser Arg Ser
225                 230                 235                 240

Asp Pro Thr Glu Gln Pro Ser Gly Leu Gly Pro Gln Leu Ala Arg Lys
                245                 250                 255

Arg Gly Leu Val Ala Trp Val Val Ser Asn Trp Asn Glu His Gln Ala
            260                 265                 270

Arg Val Arg Tyr Tyr His Gln Leu Ser Arg His Val Ser Val Asp Val
            275                 280                 285

Phe Gly Arg Thr Gly Pro Gly Arg Pro Val Pro Ala Ile Gly Leu Leu
290                 295                 300

His Thr Val Ala Arg Tyr Lys Phe Tyr Leu Ala Phe Glu Asn Ser Arg
305                 310                 315                 320

His Val Asp Tyr Ile Thr Glu Lys Leu Trp Arg Asn Ala Phe Leu Ala
                325                 330                 335

Gly Ala Val Pro Val Val Leu Gly Pro Asp Arg Ala Asn Tyr Glu Arg
            340                 345                 350

Phe Val Pro Arg Gly Ala Phe Ile His Val Asp Asp Phe Pro Asn Ala
            355                 360                 365

Ala Ser Leu Ala Ala Tyr Leu Leu Phe Leu Asp Arg Asn Val Ala Val
            370                 375                 380

Tyr Arg Arg Tyr Phe Arg Trp Arg Arg Ser Phe Ala Val His Ile Thr
385                 390                 395                 400

Ser Phe Trp Asp Glu Gln Trp Cys Arg Thr Cys Gln Ala Val Gln Thr
                405                 410                 415

Ser Gly Asp Gln Pro Lys Ser Ile His Asn Leu Ala Asp Trp Phe Gln
            420                 425                 430

Arg

<210> SEQ ID NO 12
<211> LENGTH: 355
<212> TYPE: PRT
<213> ORGANISM: Gallus gallus

<400> SEQUENCE: 12

Met Glu Leu Gly Pro Arg Trp Ser Pro Ala Ala Arg Pro Gly Cys Pro
1               5                   10                  15

Arg Arg Trp Arg Arg Arg Trp Ala Leu Leu Gly Ala Leu Leu Gly Ala
                20                  25                  30

Ala Leu Ala Leu Tyr Val Cys Val Arg Glu Leu Arg Arg Gly Ser
            35                  40                  45

Ala Ala Gly Arg Pro Glu Gly Glu Val Thr Val Leu Leu Trp Trp Glu
50                  55                  60

Pro Phe Gly Arg Pro Trp Arg Pro Ala Asp Cys Arg Arg Arg Tyr Asn
65                  70                  75                  80

```
Ile Thr Gly Cys Leu Leu Ser Ala Asp Arg Gly Arg Tyr Gly Glu Ala
                85                  90                  95

Arg Ala Val Leu Phe His His Arg Asp Leu Ala Leu His Gly Arg Gln
            100                 105                 110

Gly Leu Pro Arg Gly Pro Pro Arg Pro Arg Gln Arg Trp Val Trp
        115                 120                 125

Met Asn Phe Glu Ser Pro Ser His Ser Pro Gly Leu Arg Gly Leu Ala
    130                 135                 140

Gly Leu Phe Asn Trp Thr Met Ser Tyr Arg Arg Asp Ser Asp Val Phe
145                 150                 155                 160

Val Pro Tyr Gly Tyr Leu Tyr Glu Pro Pro Ser Pro Arg Pro Phe Val
                165                 170                 175

Leu Pro Arg Lys Ser Arg Leu Val Ala Trp Val Ile Ser Asn Trp Asn
            180                 185                 190

Glu Glu His Ala Arg Val Arg Tyr Tyr Arg Gln Leu Lys Glu His Leu
        195                 200                 205

Pro Ile Asp Val Tyr Gly Ala Arg Gly Met Ala Leu Leu Glu Gly Ser
    210                 215                 220

Val Val Lys Thr Val Ser Ala Tyr Lys Phe Tyr Leu Ala Phe Tyr Asn
225                 230                 235                 240

Ser Gln His Thr Asp Tyr Ile Thr Lys Lys Leu Trp Lys Asn Ala Phe
                245                 250                 255

Ala Ala Ser Ala Val Pro Val Val Leu Gly Pro Arg Arg Ala Asn Tyr
            260                 265                 270

Glu Arg Phe Ile Pro Ala Asp Ser Phe Ile His Val Asp Asp Phe Pro
        275                 280                 285

Ser Pro Arg Leu Leu Ala Thr Tyr Leu Lys Phe Leu Asp Lys Asn Lys
    290                 295                 300

Pro Ser Tyr Arg Arg Tyr Pro Ala Trp Arg Asn Lys Tyr Glu Val His
305                 310                 315                 320

Val Thr Ser Phe Trp Asp Glu His Tyr Cys Lys Val Cys Glu Ala Val
                325                 330                 335

Arg Thr Ala Gly Asn Gln Leu Lys Thr Val Gln Asn Leu Ala Gly Trp
            340                 345                 350

Phe Glu Ser
       355

<210> SEQ ID NO 13
<211> LENGTH: 36
<212> TYPE: PRT
<213> ORGANISM: Gallus gallus

<400> SEQUENCE: 13

Leu Gln Val Glu His Glu Asp Leu Gln Val Glu His Gly Asp Leu Gln
 1               5                  10                  15

Glu Glu His Gly Asp Leu Gln Val Glu His Asp Leu Gln Val Glu
            20                  25                  30

His Gly Asp Leu
        35

<210> SEQ ID NO 14
<211> LENGTH: 36
<212> TYPE: PRT
<213> ORGANISM: Helicobacter pylori

<400> SEQUENCE: 14
```

-continued

```
Leu Arg Val Asn Tyr Asp Asp Leu Arg Ile Asn Tyr Asp Asp Leu Arg
 1               5                  10                  15

Val Asn Tyr Asp Asp Leu Arg Val Asn Tyr Glu Arg Leu Leu Ser Lys
                20                  25                  30

Arg Thr Pro Leu
            35
```

<210> SEQ ID NO 15
<211> LENGTH: 36
<212> TYPE: PRT
<213> ORGANISM: Gallus gallus

<400> SEQUENCE: 15

```
Leu Gln Glu Glu His Gly Asp Leu Gln Glu Glu His Gly Asp Leu Gln
 1               5                  10                  15

Val Glu His Glu Asp Leu Gln Val Glu His Gly Asp Leu Gln Val Glu
                20                  25                  30

His Gly Asp Leu
            35
```

<210> SEQ ID NO 16
<211> LENGTH: 36
<212> TYPE: PRT
<213> ORGANISM: Arabidopsis thaliana

<400> SEQUENCE: 16

```
Leu Glu Lys Asp Tyr Gly Val Leu Lys Thr Gln Tyr Asp Ser Leu Arg
 1               5                  10                  15

His Asn Phe Asp Ser Leu Arg Arg Asp Asn Glu Ser Leu Leu Gln Glu
                20                  25                  30

Ile Ser Lys Leu
            35
```

<210> SEQ ID NO 17
<211> LENGTH: 36
<212> TYPE: PRT
<213> ORGANISM: Pseudomonas putida

<400> SEQUENCE: 17

```
Ala Arg Ile Ile Phe Asp Gly Leu Tyr Glu Phe Val Gly Leu Leu Asp
 1               5                  10                  15

Ala His Gly Asn Val Leu Glu Val Asn Gln Val Ala Leu Glu Gly Gly
                20                  25                  30

Gly Ile Thr Leu
            35
```

<210> SEQ ID NO 18
<211> LENGTH: 36
<212> TYPE: PRT
<213> ORGANISM: Arabidopsis thaliana

<400> SEQUENCE: 18

```
Leu Glu Thr Glu Tyr Asn Ile Leu Arg Gln Asn Tyr Asp Asn Leu Ala
 1               5                  10                  15

Ser Gln Phe Glu Ser Leu Lys Lys Glu Lys Gln Ala Leu Val Ser Glu
                20                  25                  30

Leu Gln Arg Leu
            35
```

<210> SEQ ID NO 19

-continued

```
<211> LENGTH: 36
<212> TYPE: PRT
<213> ORGANISM: Nicotiana tabacum

<400> SEQUENCE: 19
```

Leu Ala Ile Gln Val Gln Ser Leu Thr Ala Glu Asn Asn Thr Leu Lys
1               5                   10                  15

Ser Glu Ile Asn Lys Leu Met Glu Asn Ser Glu Lys Leu Lys Leu Glu
            20                  25                  30

Asn Ala Ala Leu
        35

```
<210> SEQ ID NO 20
<211> LENGTH: 36
<212> TYPE: PRT
<213> ORGANISM: Petroselium crispum

<400> SEQUENCE: 20
```

Leu Ala Ile Lys Val Asp Ser Leu Thr Ala Glu Asn Met Ala Leu Lys
1               5                   10                  15

Ala Glu Ile Asn Arg Leu Thr Leu Thr Ala Glu Lys Leu Thr Asn Asp
            20                  25                  30

Asn Ser Arg Leu
        35

```
<210> SEQ ID NO 21
<211> LENGTH: 126
<212> TYPE: DNA
<213> ORGANISM: Helicobacter pylori
<220> FEATURE:
<221> NAME/KEY: CDS
<222> LOCATION: (2)...(115)

<400> SEQUENCE: 21
``` t tat aag aat gtc tct caa acc gct aaa gag ttt aaa gac cct cat aat    49
  Tyr Lys Asn Val Ser Gln Thr Ala Lys Glu Phe Lys Asp Pro His Asn
  1               5                   10                  15 ttt gtt tta ggg gct aat atc gct ggt ttt aga aaa gta gcg tct gcg     97
Phe Val Leu Gly Ala Asn Ile Ala Gly Phe Arg Lys Val Ala Ser Ala
            20                  25                  30 atg ata gcg caa ggg gtt tagtttaccc c                               126
Met Ile Ala Gln Gly Val
        35

```
<210> SEQ ID NO 22
<211> LENGTH: 38
<212> TYPE: PRT
<213> ORGANISM: Helicobacter pylori

<400> SEQUENCE: 22
```

Tyr Lys Asn Val Ser Gln Thr Ala Lys Glu Phe Lys Asp Pro His Asn
1               5                   10                  15

Phe Val Leu Gly Ala Asn Ile Ala Gly Phe Arg Lys Val Ala Ser Ala
            20                  25                  30

Met Ile Ala Gln Gly Val
        35

```
<210> SEQ ID NO 23
<211> LENGTH: 20
<212> TYPE: DNA
<213> ORGANISM: Artificial Sequence
<220> FEATURE:
<223> OTHER INFORMATION: degenerate primer
```

-continued

```
<220> FEATURE:
<221> NAME/KEY: misc_feature
<222> LOCATION: (1)...(20)
<223> OTHER INFORMATION: n = A,T,C or G

<400> SEQUENCE: 23
ttytayctng cnttygaraa                                               20

<210> SEQ ID NO 24
<211> LENGTH: 20
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: (1)...(20)
<223> OTHER INFORMATION: n = A,T,C or G

<400> SEQUENCE: 24
aartcrtcna crtgnagraa                                               20

<210> SEQ ID NO 25
<211> LENGTH: 7
<212> TYPE: PRT
<213> ORGANISM: Helicobacter pylori

<400> SEQUENCE: 25

Asp Asp Leu Arg Val Asn Tyr
1               5

<210> SEQ ID NO 26
<211> LENGTH: 7
<212> TYPE: PRT
<213> ORGANISM: Helicobacter pylori

<400> SEQUENCE: 26

Asn Asn Leu Arg Ala Asp Tyr
1               5

<210> SEQ ID NO 27
<211> LENGTH: 7
<212> TYPE: PRT
<213> ORGANISM: Helicobacter pylori
<220> FEATURE:
<221> NAME/KEY: VARIANT
<222> LOCATION: 5
<223> OTHER INFORMATION: Xaa = Val or Ile

<400> SEQUENCE: 27

Asp Asp Leu Arg Xaa Asn Tyr
1               5
```

NUCLEIC ACIDS ENCODING α-1,3 FUCOSYLTRANSFERASES AND EXPRESSION SYSTEMS FOR MAKING AND EXPRESSING THEM

This application is a divisional of U.S. patent application Ser. No. 09/092,315, filed Jun. 5, 1998 now U.S. Pat. No. 6,399,337 which claims priority to U.S. Provisional Patent Application Serial No. 60/048,857, filed Jun. 6, 1997. All applications are incorporated herein by reference.

FIELD OF THE INVENTION

The present invention relates generally to the field of α1,3-fucosyltransferases and, more specifically, to α1,3-fucosyltransferase polypeptides which are transmembrane segment-free.

BACKGROUND OF THE INVENTION

*Helicobacter pylori* is an important human pathogen which causes both gastric and duodenal ulcers and has also been associated with gastric cancer and lymphoma. This microorganism has been shown to express cell surface glycoconjugates including Lewis X, Lewis Y, and sialyl Lewis X. These bacterial oligosaccharides are structurally similar to tumor-associated carbohydrate antigens found in mammals.

The presence of *H. pylori* isoiate has been associated with an increased risk for development of gastric cancer (Wirth, H.-P., Yang, M., Karita, M., and Blaser, M. J. (1996) *Infect. Immun.* 64, 4598–4605). This pathogen is highly adapted to colonize human gastric mucosa and may remain in the stomach with or without causing symptoms for many years. Although *H. pylori* elicits local as well as systemic antibody responses, it escapes elimination by the host immune response due to its sequestered habitation within human gastric mucosa. Another mechanism by which *H. pylori* may protect itself from the action of the host immune response is the production of surface antigens mimicking those in the host.

In mammalian cells the enzyme α(1,3/1,4)-fucosyltransferase (namely FucT) catalyzes the last step in the synthesis of two carbohydrate structures, Galβ 1–4 [Fucα1–3] GlcNAc (Lewis X, $Le^x$ for short) or NeuAcα2–3-Galβ 1–4[Fucα1–3]GlcNAc (sialyl Lewis X, $sLe^x$ for short). (Lowe et al., 1990, Cell 57: 475–484.; Kukowska-Latallo et al., 1990, Genes & Development 4:1288–1303.) Cell surface α(1,3)- and α(1,2)-fucosylated oligosaccharides, that is, Lewis X ($Le_x$), sialyl Lewis X ($sLe_x$) and Lewis Y ($Le^y$), are present on both eukaryotic and microbial cell surfaces. In mammals, $Le^x$ is a stage-specific embryonic antigen however, $Le^x$, $sLe^x$ and $Le^y$ are also regarded as tumor-associated markers. The biological functions of these bacterial oligosaccharide structures are not fully understood. It has been suggested that such glycoconjugates produced by *H. pylori*, may mimic host cell antigens and could mask the bacterium from the host immune response. It is also possible that these bacterial Lewis antigens could down regulate the host T-cell response. Therefore, production of such antigens may contribute to colonization and long-term infection of the stomach by *H. pylori*.

Presently, use of carbohydrates as potential therapeutic drugs has become popular in the field of medical chemistry. In addition, qualitative and quantitative carbohydrates including $Le^x$, $Le^y$ and $sLe^x$ are also required as reagents for assaying the enzymes which are involved in the biosynthesis of glycoconjugates in cells. $Le^x$, $Le^y$ and $sLe^x$ products which are commercially available are chemically synthesized. However, synthesis of these products gives rise to several limitations such as time-consuming, complicated procedures and low yields. Although several mammalian fucosyltransferases have been cloned and expressed, enzymatic synthesis of $Le^x$, $Le^y$ and $sLe^x$ products for a commercial purpose has not been reported.

SUMMARY OF THE INVENTION

The present invention is based on the discovery of a novel α1,3-fucosyltransferase polypeptide and gene which encodes the polypeptide. The present invention includes a novel nucleic acid sequence of α1,3-fucosyltransferase polypeptide which is useful in the detection and synthesis of α1,3-fucosyltransferase polypeptide.

In another embodiment, the invention provides a method of using the novel α1,3-fucosyltransferase to synthesize oligosaccharides such as $Le^x$, $Le_y$ and $sLe^x$.

In another embodiment the invention provides the novel polypeptide of α1,3-fucosyltransferase which is useful in the development of antibodies to α1,3-fucosyltransferase.

In another embodiment, the novel polypeptide of α1,3-fucosyltransferase has a carboxyl terminal ~100 amino acids in length having therein a heptad repeat of $X_1X_2LRX_3X_4Y$, wherein $X_1$ is D or N; $X_2$ is D or N; $X_3$ is I, V or A; $X_4$ is N or D. In another embodiment, the α1,3-fucosyltransferase is a peptide selected from SEQ ID NO:1, SEQ ID NO:2, and SEQ ID NO:3. In another embodiment the α1,3-fucosyltransferase may have a variable number of heptad repeats.

Further provided is a method for producing α1,3-fucosyltransferase. The method involves the step of culturing a gene expression system which comprises a host cell which has been recombinantly modified with a polynucleotide encoding α1,3-fucosyltransferase or a portion thereof and harvesting the α1,3-fucosyltransferase. A preferred embodiment of the method is directed to the use of the claimed genetic expression system which produces α1,3-fucosyltransferase.

These and many other features and attendant advantages of the present invention will become better understood by reference to the following detailed description of the invention when taken in conjunction with the Examples.

ABBREVIATIONS

The abbreviation used are: FucT, α1,3-fucosyltransferase unless specified otherwise; $Le^x$, Lewis X; $sLe^x$, sialyl-Lewis X; $Le^y$, Lewis Y; nt, nucleotide (s); kb, kilobase (s); aa, amino acid (s); PCR, polymerase chain reaction; ORF, open reading frame; RSB, a ribosomal binding site; LPS, lipopolysaccharides; HD-Zip, homeodomain-leucine zipper; bZip, basic region-zipper; LacNAc-R, Galβ1–4GlcNAcβ-O—$(CH_2)_8$COOMe; Galβ1–3GlcNAc-R, Galβ1–3GlcNAcbβ-O—$(CH^2)^8$COOMe; LacNAc-TMR, Galβ1–4GlcNAcβ-O—$(CH_2)_8$CO—$NHCH_2CH_2$NH-TMR; Phenyl-Gal, phenyl-β-galactoside.

BRIEF DESCRIPTION OF THE DRAWINGS

FIG. 2A-1 and FIG. 2A-2 show nucleotide (SEQ ID NO: 4) and deduced amino acid (SEQ ID NO:1) sequences of *H. pylori* fucT gene. Also shown are the nucleotide (SEQ ID NO:21) and deduced amino acid (SEQ ID NO:22) sequences of the C-terminal sequence of a putative glutamate dehydrogenase. A Shine-Dalgarno (SD) sequence, the Kozak's consensus context, putative −10 and −35 regions, an asymmetric inverted repeat and a putative transcription terminator are indicated in the nucleotide sequence. Putative asparagine-linked glycosylation sites are underlined in the amino acid sequence. Primers used for construction of pBKHp763fucT38 and pBKHp763fucT39 are located by arrow bars.

FIG. 3A-1 and FIG. 3A-2 show representative sequence alignment of the HpFucT (amino acid residues 1–372 of SEQ ID NO:1) with eukaryotic α-1,3-fucosyltransferases using the program of Pileup (the GCG package, version 8.0). BfucT3=bovine FucT III (SEQ ID NO:9); HfucT6=human FucT VI (SEQ ID NO:10); MfucT4=mouse FucT VI (SEQ ID NO:11); CfucT1=chicken FucT1 (SEQ ID NO:12). Underlined residues represent the proposed transmembrane segment within the respective FucTs. Identical residues within all the aligned proteins are denoted by both asterisks and bold type. Corresponding residues partially conserved by HpFucT and other FucTs are indicated by bold type alone.

FIG. 3B, shows a sequence comparison of the direct repeat region of HpFucT (SEQ ID NO:14) with the leucine zipper motifs within the chicken EAP-300 protein, HD-Zip proteins, and bZip proteins. Conserved leucines among all the compared proteins are marked by asterisks and bold type. Degrees of sequence identity and similarity (including the conservative replacement) between HpFucT and ATHD-Zip proteins are given on the right in panel B. ATHD-Zip, *Arabidoposis thaliana* homeobox-leucine zipper proteins, ATHB-6 (SEQ ID NO:16) and ATHB-7 (SEQ ID NO:18); EAP-300 is a developmentally regulated embryonal protein (SEQ ID NOs:13 (top) and 15 (bottom)); TAF-1, is a tobacco transcription activator 1 (SEQ ID NO:19); CPRF1, is a common plant regulatory factor isolated from parsley (SEQ ID NO:20); TodS, is a histidine kinase in *Pseudomonas putida* F1 (SEQ ID NO:17). Numbers in panels A and B indicate the aligned regions corresponding to the respective proteins.

FIG. 5 shows graphical analysis of reaction mixtures containing the membrane fraction of cells harboring pBKHp763fucT39 by capillary electrophoresis with laser-induced fluorescence detection. FIG. 5C shows separation of nine standard TMR oligosaccharides found in mammalian metabolism, LacNAcβ-(1), Fucα1→2Galβ1→4GlcNAcβ- (2), Galβ→4[Fucα1→3]GlcNAcβ- (3), Fucα1→2Galβ1→4[Fucα1→3]GlcNAcβ- (4), GlcNAcβ- (5), linker arm- (6), NeuAcα2→6LacNAcβ- (7), NeuAcα2→3LacNAcβ- (8), NeuAcα2→3Galβ1→4[Fucα1→3]GlcNAcβ-TMR (9).

FIG. 6A and FIG. 6B show the amino acid sequence comparison among HpFuc-Ts from different *H. pylori* strains. HpFuc-Ts: 26695A (SEQ ID NO:5) and 26695B (SEQ ID NO:6) from strain 26695; 1182 from UA1182 (SEQ ID NO:2); 763 from NCTC11639 (SEQ ID NO:7); 11637 from NCTC11637 (SEQ ID NO:8); and 802 from UA802 (SEQ ID NO: 3). The position leading to the frameshift is indicated by a ↑.

DETAILED DESCRIPTION OF THE INVENTION

The present invention relates to novel purified α1,3-fucosyltransferase polypeptides, polynucleotides which encode the α1,3-fucosyltransferase, and the use of the α1,3-fucosyltransferase gene and α1,3-fucosyltransferase polypeptides in the production of biologics and in the screening of biological tissues and fluids. The invention also relates to antibodies against α1,3-fucosyltransferase polypeptides and their use in diagnosing disorders and in monitoring disease.

The α1,3-fucosyltransferase Polypeptide

Figure 2B:
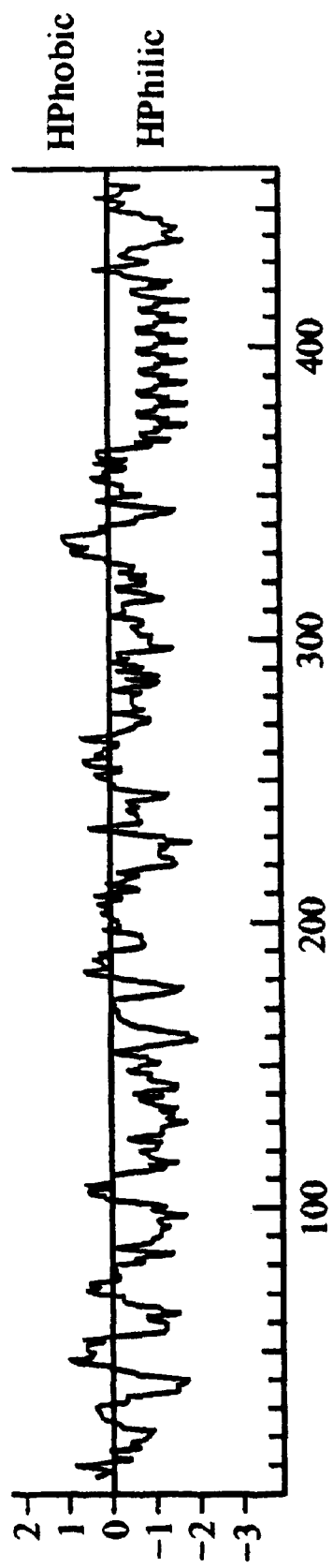
FIG. 2B, a hydropathy profile of HpFucT as predicted by the method of Kyte-Doolittle.

The amino acid sequence encoded by the α1,3-fucosyltransferase gene is shown in FIG. 2. In one embodiment, the α1,3-fucosyltransferase is transmembrane segment-free. The term "transmembrane segment-free" refers the absence of a transmembrane segment found in eukaryotic α1,3-fucosyltransferase. Absence of a transmembrane segment allows the α1,3-fucosyltransferase of the invention to be readily released from cells expressing the enzyme. Further, because the α1,3-fucosyltransferase are prokaryotically derived post-translational modifications are not made to the enzyme, unlike the eukaryotically expresses α1,3-fucosyltransferase.

Additionally, the α1,3-fucosyltransferase polypeptide may be altered by addition or deletions of peptide sequences in order to modify its activity. For example, polypeptide sequences may be fused to the α1,3-fucosyltransferase polypeptide in order to effectuate additional enzymatic activity. Alternatively, amino acids may be deleted to remove or modify the activity of the protein. The protein may be modified to lack α1,3-fucosyltransferase enzymatic activity but yet retain its structural three-dimensional structure. Such modification would be useful in the development of antibodies against α1,3-fucosyltransferase polypeptide as described more fully below.

Another embodiment relates to the direct repeats of seven amino acid residues proximal to the C-terminus. These heptad repeats have the structure: $X_1X_2LRX_3X_4Y$, wherein $X_1$ and $X_2$ are independently D or N; $X_3$ is I, V or A; $X_4$ is N or D The number of heptad repeats which potentially constitute a leucine zipper (L-Zip) may be varied (FIG. 6). Another embodiment is directed to the amino acid substitutions introduced into these heptad repeats.

In yet another embodiment, the invention includes aspects of the enzymatic activity of α1,3-fucosyltransferase, wherein the α1,3-fucosyltransferase polypeptide lacks α1,4-fucosyltransferase or α1,2-fucosyltransferase activity or lacks both α1,2-fucosyltransferase and α1,4-fucosyltransferase activity The α1,3-fucosyltransferase gene product may include those proteins encoded by the α1,3-fucosyltransferase gene sequences described in the section below. Specifically, α1,3-fucosyltransferase gene products, sometimes referred to herein as "α1,3-fucosyltransferase polypeptides", may include α1,3-fucosyltransferase gene product encoded by an α1,3-fucosyltransferase gene sequence shown in FIG. 2 and SEQ ID NO:4. Thus, the term "α1,3-fucosyltransferase polypeptide" includes full length expression as well as polypeptides, such as smaller peptides, which retain a biological activity of the full length product, such as α1,3-fucosyltransferase activity.

In addition, α1,3-fucosyltransferase gene products may include proteins or polypeptides that represent functionally equivalent gene products, for example and not by way of limitation, the sequences of SEQ ID NO:1, SEQ ID NO:2 and SEQ ID NO: 3. Such an equivalent α1,3-fucosyltransferase gene product may contain deletions, additions or substitutions of amino acid residues within the amino acid sequence encoded by the α1,3-fucosyltransferase gene sequences described above, but which results in a silent change, thus producing a functionally equivalent α1,3-fucosyltransferase gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a polypeptide capable of exhibiting a substantially similar in vivo activity as the endogenous α1,3-fucosyltransferase gene products encoded by the α1,3-fucosyltransferase gene sequences described above, as judged by any of a number of criteria, including but not limited to antigenicity, i.e., the ability to bind to an anti-α1,3-fucosyltransferase antibody, immunogenicity, i.e., the ability to generate an antibody which is capable of binding a α1,3-fucosyltransferase protein or polypeptide, as well as enzymatic activity.

A substantially purified α1,3-fucosyltransferase protein, polypeptide, and derivative (including a fragment) is substantially free of other proteins, lipids, carbohydrates, nucleic acids, and other biological materials with which it is naturally associated. For example, a substantially purified functional fragments of α1,3-fucosyltransferase polypeptide can be at least 60%, by dry weight, the molecule of interest. One skilled in the art can purify functional fragment of α1,3-fucosyltransferase protein using standard protein purification methods and the purity of the polypeptides can be determined using standard methods including, e.g., polyacrylamide gel electrophoresis (e.g., SDS-PAGE), column chromatography (e.g., high performance liquid chromatography), and amino-terminal amino acid sequence analysis.

Included within the scope of the invention are α1,3-fucosyltransferase proteins, polypeptides, and derivatives (including fragments) which are differentially modified during or after translation. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. Additionally, the composition of the invention may be conjugated to other molecules to increase their water-solubility (e.g., polyethylene glycol), half-life, or ability to bind targeted tissue.

Furthermore, nonclassical amino acids or chemical amino acid analogs can be introduced as a substitution or addition into the α1,3-fucosyltransferase polypeptide sequence. Nonclassical amino acids include, but are not limited to, the D-isomer of the common amino acids, α-amino isobutyric acid, 4-aminobutyric acid, Abu, 2-amino butyric acid, γ-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids, such as β-methyl amino acids, α-methyl amino acids, Nα-methyl amino acids, and amino acid analogs in general. Furthermore, the amino acid can be D (dextrorotary) or L (levorotary).

While random mutations can be made to α1,3-fucosyltransferase DNA (using random mutagenesis techniques known to those skilled in the art) and the resulting mutant α1,3-fucosyltransferase polypeptides tested for activity, site-directed mutation of the α1,3-fucosyltransferase coding sequence can be engineered (using site-directed mutagenesis techniques well known to those skilled in the art) to create mutant α1,3-fucosyltransferase polypeptides with increased functional characteristics.

Peptides corresponding to one or more domains of the α1,3-fucosyltransferase protein, truncated or deleted α1,3-fucosyltransferase proteins as well as fusion proteins in which the full length α1,3-fucosyltransferase proteins, polypeptides or derivatives (including fragments), or truncated α1,3-fucosyltransferase, is fused to an unrelated protein are also within the scope of the invention and can be designed on the basis of the α1,3-fucosyltransferase nucleotide and α1,3-fucosyltransferase amino acid sequences disclosed in this section and the section above. The fusion protein may also be engineered to contain a cleavage site located between a α1,3-fucosyltransferase sequence and the non-α1,3-fucosyltransferase protein sequence, so that the α1,3-fucosyltransferase polypeptide may be cleaved away from the non-α1,3-fucosyltransferase moiety. Such fusion proteins or polypeptides include but are not limited to IgFc fusion which may stabilize the α1,3-fucosyltransferase protein in vivo; or fusion to an enzyme, fluorescent protein, or luminescent protein which provide a marker function.

The α1,3-fucosyltransferase polypeptide may be produced by recombinant DNA technology using techniques well known in the art. Thus, methods for preparing the α1,3-fucosyltransferase polypeptides of the invention by expressing nucleic acid containing α1,3-fucosyltransferase gene sequences are described herein. Method which are well known to those skilled in the art can be used to construct expression vectors containing α1,3-fucosyltransferase coding sequences and appropriate transcriptional translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding α1,3-fucosyltransferase polypeptide may be chemically synthesized using, for example, synthesizers. See, for example, the techniques described in "Oligonucleotide Synthesis", 1984, Gait, M. J. ed., IRL Press, Oxford, which is incorporated by reference herein in its entirety. The use of such synthetic peptide fragments of α1,3-fucosyltransferase for generating polyclonal antibodies is described below.

The α1,3-fucosyltransferase Gene

The α1,3-fucosyltransferase gene is a novel gene (FIG. 2) whose expression is found in *H. pylori*. Nucleic acid sequences of the identified α1,3-fucosyltransferase genes are described herein. As used herein, "α1,3-fucosyltransferase gene" refers to (a) a gene containing the DNA sequence shown in FIG. 2; (b) any DNA sequence that encodes the amino acid sequence shown in FIG. 2, SEQ ID NO: 1, SEQ ID NO: 2 or SEQ ID NO: 3; (c) any DNA sequence that hybridizes to the complement of the coding sequences shown in FIG. 2, SEQ ID NO: 1, SEQ ID NO: 2 or SEQ ID NO: 3 under stringent conditions, e.g., hybridization to filter-bound DNA in 0.5 M $NaHPO_4$, 7%, sodium dodecyl sulfate (SDS), 1 mM EDTA at 65° C., and washing in 0.1×SSC/0.1% SDS at 68° C. (Ausubel F. M. et al., eds., 1989, *Current Protocols in Molecular Biology*, Vol. 1, Green Publishing Associates, Inc., and John Willey & Sons, Inc., New York, at p. 2.10.3) and encodes a gene product functionally equivalent to a gene product encoded by sequences shown in FIG. 2; and/or (d) any DNA sequence that hybridizes to the complement of the coding sequences disclosed herein (as shown in FIG. 2), under less stringent conditions, such as moderately stringent conditions, e.g., washing in 0.2% SSC/0.1% SDS at 42° C. (Ausubel et al., 1989, supra), and encodes a gene product functionally equivalent to a gene product encoded by sequences shown in FIG. 2.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent condition may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act at α1,3-fucosyltransferase gene regulation and/or as antisense primers in amplification reactions of α1,3-fucosyltransferase gene nucleic acid sequences. Further, such sequences may be used as part of ribozyme and/or triple helix sequences, also useful for α1,3-fucosyltransferase gene regulation. Still further, such molecules may be used as components of diagnostic methods whereby the presence of a pathogen or metastatic tumor cell may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression.

The invention includes fragments of any of the DNA sequences disclosed herein. Fragments of the α1,3-fucosyltransferase gene corresponding to coding regions of particular domains, or in which one or more of the coding regions of the domains is deleted (e.g., the sequence encoding the c-terminal 101 amino acids as shown in FIG. 2), are especially useful. Such α1,3-fucosyltransferase gene fragments may encode truncated gene products that retain a biological activity of the full-length α1,3-fucosyltransferase polypeptide, such as α1,3-fucosyltransferase activity or immunogenicity. The invention also includes mutant α1,3-fucosyltransferase genes encoding substitutions of amino acids as described below.

In addition to the gene sequences described above, homologs of such sequences, as may, for example, be present in other species, including humans, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

The α1,3-fucosyltransferase gene and its homologs can be obtained from other organisms thought to contain α1,3-fucosyltransferase activity. For obtaining cDNA, tissues and cells in which α1,3-fucosyltransferase is expressed are optimal. Tissues which can provide a source of genetic material for α1,3-fucosyltransferase and its homologs, therefore, include intestinal mucosal cells and tumorigenic cells.

For example, the isolated α1,3-fucosyltransferase gene sequences may be labeled and used to screen a cDNA library constructed from mRNA obtained from the organism of interest. The hybridization conditions used should be of a lower stringency when the cDNA library is derived from an organism different from the type of organisms from which the labeled sequence was derived. Alternatively, the labeled fragment may be used to screen a genomic library derived from the organism of interest, again, using appropriately stringent condition. Low stringency conditions are well known in the art, and will vary predictably depending on the specific organism from which the library and the labeled sequences are derived. For guidance regarding such condition see, for example, Sambrook et al., 1989, *Molecular Cloning, a Laboratory Manual*, Cold Springs Harbor Press, N.Y.; and Ausubel et al., 1989, *Current Protocols in Molecular Biology*, Green Publishing Associates and Wiley Interscience, N.Y.

Further, a previously unknown α1,3-fucosyltransferase gene type sequence may be isolated by performing PCR using two degenerate oligonucleotide primer pools designed on the basis of amino acid sequence within the gene of interest. The template for the reaction may be cDNA obtained by reverse transcription of mRNA prepared from human or non-human cell lines or tissue known or suspected to express a α1,3-fucosyltransferase gene.

The PCR product may be subcloned and sequenced to ensure that the amplified sequences represent the sequences of α1,3-fucosyltransferase gene-like nucleic acids sequences. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanidines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the α1,3-fucosyltransferase gene identified is the normal, or wild type, gene, this gene may be used to isolate mutant alleles of the gene. Mutant alleles may be isolated from individuals either known or proposed to have a genotype which contributes to intestinal mucosal disease and/or tumorigenicity. Mutant alleles and mutant allele products may then be utilized in the therapeutic and diagnostic systems described below.

A cDNA of the mutant gene may be isolated, for example by PCR. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically the 5' end of the normal gene. Using these primers, the product is then amplified via PCR, cloned into a suitable vector, and subjected to DNA sequences analysis through methods known in the art. By comparing the DNA sequence of the mutant gene to that of the normal gene, the mutation(s) responsible for the loss or alteration of function of the mutant gene product can be ascertained.

A variety of host-expression vector systems may be utilized to express the α1,3-fucosyltransferase gene coding sequences of the invention. Such host-expression systems represent vehicles by which the coding sequences of interest may be produced and subsequently purified, but also represent cells which, when transformed or transfected with the appropriate nucleotide coding sequences, exhibit the α1,3-fucosyltransferase gene product of the invention in situ. These include but are not limited to microorganisms such as bacteria (e.g., E. coli, B. subtilis) transformed with recombinant bacteriophage DNA, plasmid DNA or cosmid DNA expression vectors containing α1,3-fucosyltransferase gene product coding sequences; yeast (e.g. Saccldaromyces, Pichia) transformed with recombinant yeast expression vectors containing the α1,3-fucosyltransferase gene product coding sequences; insect cell systems infected with recombinant virus expression vectors (e.g., baculovirus) containing the α1,3-fucosyltransferase gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing α1,3-fucosyltransferase gene product coding sequences; or mammalian cell systems (e.g., COS, SHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the α1,3-fucosyltransferase gene product being expressed. For example, when a large quantity of such a protein is to be produced, for the generation of pharmaceutical compositions of α1,3-fucosyltransferase polypeptide or for raising antibodies to α1,3-fucosyltransferase polypeptide, for example, vectors which direct the expression of high levels of fusion protein products that are readily purified may be desirable. Such vectors include, but are not limited to the E. coli expression vector pUR278 (Ruther et al., 1983, EMBO J. 2:1791), in which the α1,3-fucosyltransferase gene product coding sequence may be ligated individually into the vector in frame with the lac z coding region that a fusion protein is produced; pIN vectors (Inouye & Inouye, 1985, Nucleic Acids Res. 13:3101–3109); and the like. pGEX vectors may also be used to express foreign polypeptide as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa colifornica* nuclear polyhedrosis virus (AcNPV) is used as a vector to express foreign genes. The virus grows in *Spodoptera frugiperday* cells. The α1,3-fucosyltransferase gene coding sequence may be cloned individually into non-essential regions (for example the polyhedrin gene) of the virus and placed under the control of an AcNPV promoter. Successful insertion of α1,3-fucosyltransferase gene coding sequence will result in inactivation of the polyhedrin gene and production of non-occluded recombinant virus. These recombinant viruses are then used to infect *S. frugiperda* cells in which the inserted gene is expressed.

In mammalian host cells, a number of viral-based expression systems may be utilized. In cases where an adenovirus is used as an expression vector, the α1,3-fucosyltransferase gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing α1,3-fucosyltransferase gene product in infected hosts (See Logan & Shenk, 1984, Proc. Natl. Acad. Sci, USA 81:3655–3659). Specific initiation signals may also be required for efficient translation of inserted α1,3-fucosyltransferase gene product coding sequences. These signals include the ATG initiation codon and adjacent sequences. In cases where an entire α1,3-fucosyltransferase gene, including its own initiation codon and adjacent sequences, is inserted into the appropriate expression vector, no additional translation control signals may be needed. However, in cases where only a portion of the α1,3-fucosyltransferase gene coding sequences is inserted, exogenous translational control signals, including, the ATG initiation codon must be provided.

Transfection via retroviral vectors, naked DNA methods and mechanical methods including micro injection and electroporation may be used to provide either stably transfected host cells (i.e., host cells that do not lose the exogenous DNA over time) or transient transfected host cells (i.e., host cells that lose the exogenous DNA during cell replication and growth).

An alternative fusion protein system allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cell infected with recombinant vaccinia virus are loaded onto $Ni^{2+}$ nitriloacetic acid-agarose columns and histidine-tagged proteins are selectively eluted with imidazole-containing buffers.

The α1,3-fucosyltransferase gene products can also be expressed in transgenic animals. Animals of any species, including, but not limited to, mice, rats, rabbits, guinea pigs, pigs, micro-pigs, goats, and non-human primates may be used to generate α1,3-fucosyltransferase transgenic animals.

Expression Systems for α1,3-fucosyltransferase

The novel bacterial α1,3-fucosyltransferase encoded by the disclosed gene, and enzymatically active fragment thereof, can be used in the production of fucosylated oligosaccharides such as Lewis X, Lewis Y, and siayl Lewis X. These bacterial oligosaccharides are structurally similar to certain tumor-associated carbohydrate antigens found in mammals. These product glycoconjugates also have research and diagnostic utility in the development of assays to detect mammalian tumors.

The fucosylated oligosaccharides may be produced by any number of methods utilizing the methods and compositions described herein. Standard enzymology techniques well known in the art may be utilized to develop systems to provide fucosylated oligosaccharides (see for example the *Methods in Enzymology*, volume series published by Academic Press; and Tim Bugg, "An Introduction to Enzyme and Coenzyme Chemistry", 1997, Blackwell Sciences, Inc.).

"Substrate", as used herein, means any material or combinations of different materials, that may be acted upon by the polypeptide of the invention to give rise to fucosylated oligosaccharides, for example, and not by way of limitation, substrates may include LacNAc-R and GDP-fucose.

Cells containing and cell-free systems may be used to produce the fucosylated oligosaccharides of the present invention. Cells containing and cell-free systems will be better understood in the description and examples that follow. Such systems are useful in the development of fucosylated oligosaccharides.

The present invention provides a method for synthesizing fucosylated oligosaccharides by reacting substrates in the presence of α1,3-fucosyltransferase, capable of catalyzing the formation of the fucosylated oligosaccharides from the substrates.

The α1,3-fucosyltransferase may be used regardless of its origin as long as it is capable of producing the fucosylated oligosaccharides from the substrates. The source of the α1,3-fucosyltransferase may be derived according to the methods and compositions as described herein, for example, through protein purification from host cells transfected with an expression system as described more fully below.

The substrates are allowed to react with the α1,3-fucosyltransferase polypeptide for a sufficient time and under sufficient conditions to allow formation of the enzymatic product, e.g. $Le^x$, $Le^y$ and $sLe_x$. These conditions will vary depending upon the amounts and purity of the substrate and enzyme, whether the system is a cell-free or cellular based system. These variables will be easily adjusted by those skilled in the art. For example, the period of exposure of the enzyme to the substrate will be longer at lower temperatures, e.g., 4° C. rather than at higher temperatures.

In the methods for synthesizing the fucosylated oligosaccharides there are no restriction in terms of the timing of the addition of the substrates. The ratios of the various substrates should be in equal proportions, i.e. 1:1. The ratios of the enzyme to the substrates may be varied depending upon the rate and quantity of fucosylated oligosaccharides desired.

The method of producing the fucosylated oligosaccharides may be carried out at temperatures of 4° C. to 60° C., more specifically at 20° C. to 45° C. Additionally, a number of buffers may be used, for example, and not by way of limitation, a buffer having a pH between 6.5 and 8.0, but more preferably at pH 7.5, and in the presence of 15–30 mM $Mn^{2-}$ but more preferably at a 25 mM $Mn^{2+}$ concentration. After a desired amount of fucosylated oligosaccharides are produced the α1,3-fucosyltransferase polypeptide may be inactivated by heating, centrifugal separation, or the like. The resulting fucosylated oligosaccharides may be further purified by techniques known to those skilled in the art.

Cell containing systems for the synthesis of fucosylated oligosaccharides may include recombinatntly modified host cells according to the methods described below or may be naturally occurring cells which express α1,3-fucosyltransferase polypeptide or an enzymatically active portion thereof, so long as the cell is capable of catalyzing the synthesis of fucosylated oligosaccharides from substrates.

In the case of cell containing systems the host cell is contacted with the substrate, under conditions and for sufficient time to produce the oligosaccharide. The time and conditions will vary depending upon the host cell type and culture conditions and can be easily determined by those of skill in the art.

The invention provides a gene expression system for producing α1,3-fucosyltransferase polypeptides. The gene expression system comprises a host cell which been modified with a polynucleotide encoding α1,3-fucosyltransferase polypeptide or a portion thereof, as described above.

A preferred gene expression system of the invention involves host cell modified with a polynucleotide encoding α1,3-fucosyltransferase polypeptide or a portion thereof.

The method involves culturing a gene expression system created according to the methods described above under conditions sufficient to produce the α1,3-fucosyltransferase polypeptide. The gene expression system comprises a host cell which has been recombinantly modified with a polynucleotide encoding a α1,3-fucosyltransferase polypeptide or a portion thereof.

The method is also directed to harvesting the α1,3-fucosyltransferase polypeptide. A further step of the method involves substantially purifying the harvested α1,3-fucosyltransferase. The purified α1,3-fucosyltransferase polypeptide may be used in the synthesis of fucosylated oligosaccharides or the preparation of antibodies as described above.

Specifically disclosed herein is a gene expression system recombinantly modified with a DNA sequence containing the α1,3-fucosyltransferase gene. The sequence contains an open reading frame (ORF) of approximately 1211 base pairs which are transcribed into α1,3-fucosyltransferase product.

As used herein, the term "recombinantly modified" means introducing a polynucleotide encoding α1,3-fucosyltransferase polypeptide into a living cell or gene expression system. Usually, the polynucleotide is present in a plasmid or other vector, although modification can also occur by uptake of free α1,3-fucosyltransferase polynucleotide or numerous other techniques known in the art.

As used herein, the term "gene expression system" means a living eukaryotic or prokaryotic cell into which a gene, whose product is to be expressed, has been introduced, as described above.

As used herein, the term "harvesting" means collecting or separating from the gene expression system the product produced by the inserted polynucleotide.

Polynucleotide sequences encoding α1,3-fucosyltransferase polypeptides can be expressed by polynucleotide transfer into a suitable host cell.

"Host cells" are cells in which a vector can be propagated and its DNA expressed. A gene expression system is comprised of a host cell in which a vector was propagated and the vector's DNA expressed. The term "host cell" also includes any progeny of the subject host cell. It is understood that all progeny may not be identical to the parental cell since there may be mutations that occur during replication. However, such progeny are included when the term "host cell" is used. Host cells which are useful in the claimed gene expression system and the claimed method of producing α1,3-fucosyltransferase polypeptide include bacterial cells, yeast cells fungal cells, plant cells and animal cells.

Methods of stable transfer, meaning that the foreign DNA is continuously maintained in the host, are known in the art. In the present invention, the α1,3-fucosyltransferase polynucleotide sequences may be inserted into a recombinant expression vector. The term "recombinant expression vector" refers to a plasmid, virus or other vehicle known in the art that has been manipulated by insertion or incorporation of the α1,3-fucosyltransferase genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Biologically functional viral and plasmid DNA vectors capable of expression and replication in a host are known in the art. Such vectors are used to incorporate DNA sequences of the invention.

The method of the invention produces α1,3-fucosyltransferase polypeptide which are substantially pure. As used herein. the term "substantially pure" refers to a protein which is free of other proteins, lipids, carbohydrates or other materials with which it is naturally associated. One skilled in the art can purify α1,3-fucosyltransferase polypeptide using standard techniques for protein purification including preparative chromatography and immunological separations involving monoclinal or polyclonal antibodies. For example, the substantially pure α1,3-fucosyltransferase protein will yield a single major band of approximately 52 kD on a non-reducing polyacrylamide gel. The purity of the α1,3-fucosyltransferase polypeptide can also be determined by amino-terminal amino acid sequence analysis. α1,3-fucosyltransferase polypeptide include functional fragments of the polypeptide, as long as biological activity remains, such as α1,3-fucosyltransferase enzymatic activity. Accordingly, the invention includes a gene expression system and a method of producing α1,3-fucosyltransferase polypeptide which produce smaller peptides containing the enzymatic activity of a 1,3-fucosyltransferase.
Production of α1,3-fucosyltransferase.

Production of α1,3-fucosyltransferase from the gene expression system of the invention is achieved by culturing a gene expression system comprising a host cell recombinantly modified with a polynucleotide encoding α1,3-fucosyltransferase polypeptide or an enzymatically active portion thereof and harvesting the α1,3-fucosyltransferase polypeptide. The method further comprises substantially purifying the harvested α1,3-fucosyltransferase polypeptide using protein purification protocols well known in the art (Current Protocols in Molecular Biology, Chapter 10, eds. Ausubel, F. M. et al., 1994).

The method for producing α1,3-fucosyltransferase polypeptide involves culturing the gene expression system of the invention under conditions of continuous culture, such as, but not restricted to, "fed-batch cultures" or continuous perfusion cultures. Other continuous culture systems which find use in the present invention is set forth in Wang, G. et al. *Cytotechnology* 9:41–49, 1992; Kadouri, A. et al. *Advances in Animal Cell Biology and Technology for Bioprocesses*, pp. 327–330, Courier International, Ltd., 1989; Spier, R. E. et al. *Biotechnol. Bioeng.* 18:649–57, 1976.

TABLE 1

Enzyme activity of the *H. pylori* FucT produced in *E. coli* CSRDE3 cells with an acceptor LacNAc-R

| Sample[a] | Activity (mU)[b] | Specific activity[c] | Relative activity[d] |
|---|---|---|---|
| BKHp763fucT38 | | | |
| cytoplasm | 0 | 0 | 0 |
| membrane | 0 | 0 | 0 |
| pBKHp763fucT39 | | | |
| cytoplasm | 0.6 | 0.026 | 15% |
| membrane | 3.4 | 0.62 | 85% |
| membrane+ Triton X-100 | 4.3 | 0.77 | — |

[a]Membrane and cytoplasmic fractions were prepared from cells grown in 300 ml LB broth as described under Experimental Procedures.
[b]A milliunit of enzyme activity is expressed as the amount of the enzyme fraction which catalyzes the conversion of one nanomole of acceptor to product per minute. Numbers represent total mU obtained from each enzyme fraction.
[c]mU per mg protein.
[d]One hundred percent activity is total mU obtained from both the cytoplasmic and membrane fractions.

Antibodies to α1,3-fucosyltransferase Proteins

Antibodies that define the α1,3-fucosyltransferase gene product are within the scope of this invention, and include antibodies capable of specifically recognizing one or more α1,3-fucosyltransferase gene product epitopes. Such antibodies may include, but are not limited to, polyclonal antibodies, monoclinal antibodies, humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of α1,3-fucosyltransferase gene product in a biological sample, including, but not limited to, blood, plasma, and serum. Alternatively, the antibodies may be used as a method for the inhibition of abnormal α1,3-fucosyltransferase gene product activity. Thus, such antibodies may be utilized as part of treatment for intestinal mucosal disease, and may be used as part of diagnostic techniques whereby patients may be tested for abnormal levels of α1,3-fucosyltransferase gene products, or for the presence of abnormal forms of such proteins.

For the production of antibodies against a α1,3-fucosyltransferase gene product, various host animals may be immunized by injection with a α1,3-fucosyltransferase gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsion, keyhole limpet hemocyanin, dinitrophenol, and potentially useful human adjuvants such as BCG, interferon and other cytokines effecting immunological response.

Polyclonal antibodies are a heterogenous population of antibody molecules derived from the sera of animals immunized with an antigen, such as a α1,3-fucosyltransferase gene product, or an antigenic functional derivative thereof. In general, for the production of polyclonal antibodies, host animals such as those described above, may be immunized by injection with α1,3-fucosyltransferase gene product supplemented with adjuvants as also described above.

Monoclonal antibodies (mAbs), which are homogenous population of antibodies to a particular antigen, may be obtained by any technique which provides for the production of antibody molecules by continuous cell lines in culture. These techniques include, but are not limited to, the hybridoma technique of Kohler and Milstein, (1975, Nature 256:495–497; and U.S. Pat. No. 4,376,110), human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclinal Antibodies and Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate bioloical activity can be used. A chimeric antibody is molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against α1,3-fucosyltransferase gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclinal Fab fragments with the desired specificity.

Methods of Detecting α1,3-fucosyltransferase in Biological Samples

The antibodies described above can be used in the detection of α1,3-fucosyltransferase polypeptides in biological samples. α1,3-Fucosyltransferase polypeptide from blood or other tissue or cell type may be easily isolated using techniques which are well known to those of skill in the art. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic method for the detection of wild type or mutant α1,3-fucosyltransferase polypeptides may involve, for example, immunoassays wherein α1,3-fucosyltransferase polypeptides are detected by their interaction with an anti-α1,3-fucosyltransferase polypeptide specific antibody.

For example, antibodies, or fragments of antibodies, such as those described above, useful in the present invention may be used to quantitatively or qualitatively detect the presence of wild type or mutant α1,3-fucosyltransferase polypeptides. This can be accomplished, for example, by immunofluorescence techniques employing a fluorescently labeled antibody coupled with light microscopic, flow cytometric, or fluorimetric detection. Such techniques are especially preferred if the α1,3-fucosyltransferase polypeptides are expressed on the cell surface.

The antibodies (or fragments thereof) useful in the present invention may, additionally, be employed histologically, as in immunofluorescence or immunoelectron microscopy, for in situ detection of α1,3-fucosyltransferase polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the α1,3-fucosyltransferase polypeptide, but also its distribution in the examined tissue. Using the present invention, those skill in the art will readily perceive that any of a wide variety of histological methods (such as staining procedures) can be modified in order to achieve such in situ detection.

Immunoassays for wild type or mutant α1,3-fucosyltransferase polypeptides typically comprise incubating a biological sample, such as a biological fluid, including but not limited to blood, plasma, or blood serum, a tissue extract, freshly harvested cells, or cells which have been incubate in tissue culture, in the presence of a detectably labeled antibody capable of identifying α1,3-fucosyltransferase polypeptides, and detecting the bound antibody by any of a number of techniques well known in the art.

Detection may also be accomplished using any of a variety of other immunoassays. For example, by radioactively labeling the antibody or antibody fragments, it is possible to detect wild type or mutant α1,3-fucosyltransferase polypeptides through the use of radioimmunoassays (RIA) (see, for example, Weintraub, Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound such fluorescein isothiocyanate, rhodomine, phycoerythrin, phycocyanin, allophycocyanin and fluorescamine.

The antibody can also be detectably labeled using fluorescence emitting metals such as $^{152}$Eu. Additionally the antibody may be detected by coupling it to a chemiluminescent compound such as luminol, isoluminol, theramatic acreidinium ester and oxalate ester.

The following examples are intended to illustrate but not limit the invention. While they are typical, other procedures known to those skilled in the art may alternatively be used to illustrate the embodiments and methods of the invention.

EXAMPLE 1
Cloning of the H. pylori Fucosyltransferase (fucT) Gene

To clone the fucosyltransferase gene from H. pylori NCTC11639, degenerate primers were generated from the several regions conserved by three mammalian α1,3-fucosyltransferases, including human FucT VI, bovine FucT III and mouse FucT VI. Primer FUTF3 (5'TT[T/C]TA[TC]CT[T/C/A/G]GC[G/A/T/C]TT[T/C]GA[A/G]AA3') (SEQ ID NO:23) corresponds to residues 242–248 of human FucT VI, whereas primer FUCTR2 (5'AA[A/G]TC[A/G]TC[G/ATC]AC[A/G]TG[G/A/T/C]AG[A/G]AA3') (SEQ ID NO:24) is complementary to the sequence deduced from its residues 289–295. An expected DNA fragment of ~170 nt was PCR-amplified from chromosomal DNA of H. pylori NCTC11639 with the primer pair of FUCTF3 and FUCTR2 under a thermocycling program of 40 cycles: for the first two cycles, 1 min at 94° C., 30 sec at 40° C. and 40 sec at 72° C.; for the remaining cycles, 1 min. at 94° C., 30 sec at 50° C. and 40 sec at 72° C., followed by extension at 72° C. for 10 min. The PCR products were cloned into vector pCRT-MII (Invitrogen, San Diego, Calif.) according to the supplier's instructions. Subsequently, the inserts in recombinant plasmids were sequenced with Thermo sequenase, and their nucleotide sequences and deduced amino acid sequences were used in the search for related proteins in databases with the software program Blast included in the GCG package (Version 8.0, Genetic Computing Group, Inc., Madison, Wis.). A clone, designated pCRHpfucT3, was demonstrated to contain the insert encoding the amino acid sequence homologous to known mammalian α1,3-fucosyltransferase.

To clone a putative intact fucT gene from H. pylori, chromosomal DNA from H. pylori NCTC11639 was digested with restriction endonucleases, including Bg/II, EcoRI, BamHI, BglI-EcoRI, EcoRI-BamHI and Bg/II-BamHI, and then separated in a 1% agarose gel. DNA fragments containing the putative fucT gene were demonstrated by Southern hybridization with a [α-$^{32}$P]dCTP-labeled probe made from pCRHpfucT3 DNA. The 2.2-kb EcoR1-Bg/II and 4.5-kb EcoRI-BamHI fragments were cloned into vector pBluescript II KS- (Stratagene, La Jolla, Calif.) which was digested with EcoRI and BamHI. Two clones, pBKHpfucT8 carrying a 2.2-kb EcoR1-Bg/II fragment and pBKHpfucT31 carrying a 4.5 kb EcoRI-BamHI, were selected for further characterization.

EXAMPLE 2
Plasmid Constructs and Expression of the H. pylori fucT Gene

Figure 1:
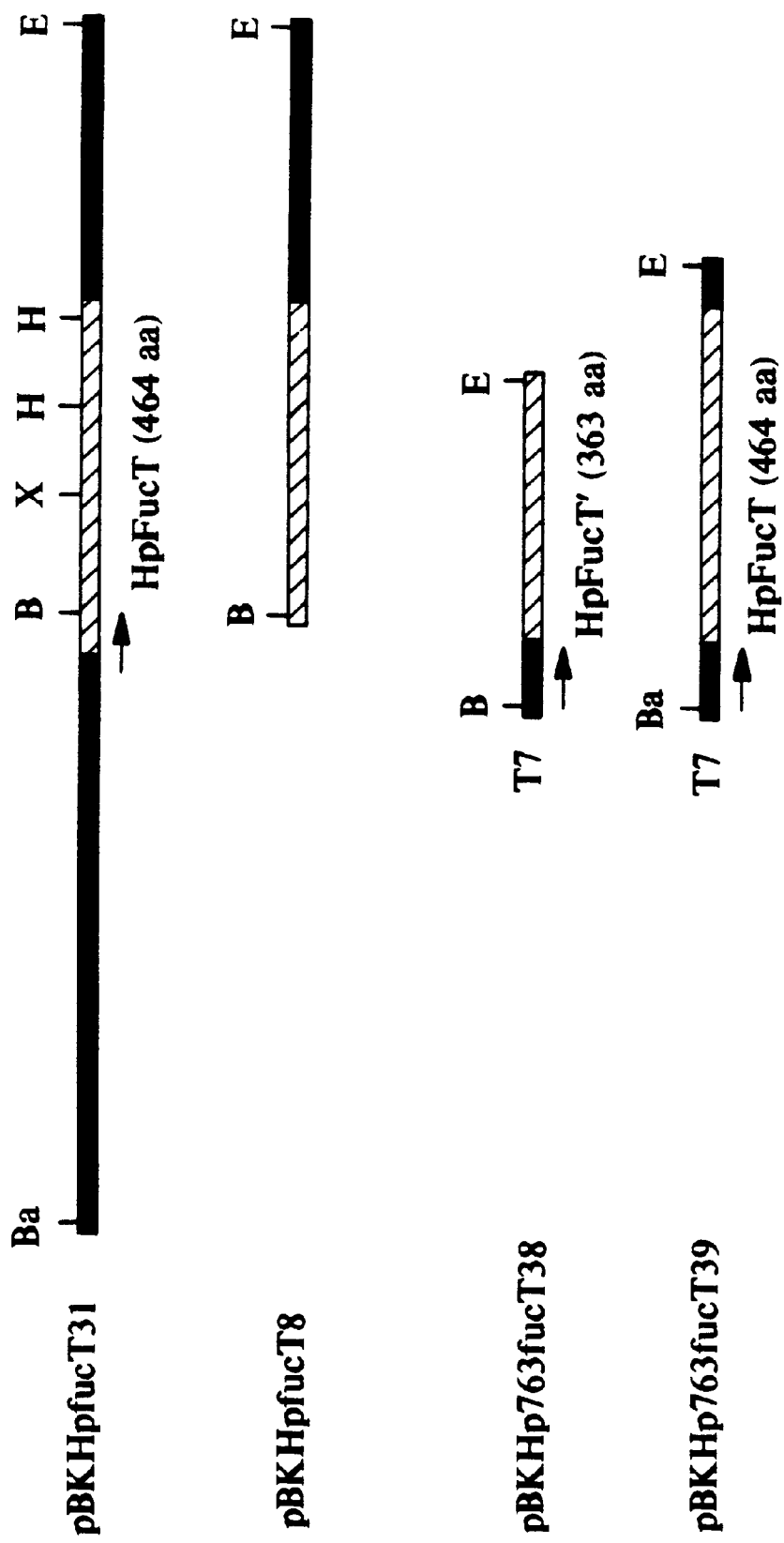
FIG. 1. Schematic representation of plasmid constructs containing an intact or partial HpfucT gene. Hatched arrow bars represent the *H. pylori* fucT genes, and the arrows point in the direction of the transcription orientation. T7 indicates the location of a T7 promoter. Restriction endonuclease sites used for subcloning are denoted. BA=BamHI; B=BglII; X=XmnI; H=HindIII; and E=EcoRI.

To construct recombinant plasmids containing an intact or partial H. pylori fucT gene, three primers were generated from the nucleotide sequence in FIG. 1: ZGE37 corresponding to nucleotides 1–19; ZGE38and ZGE39 complementary to nucleotides 1215–1233 and 1660–1679 respectively. ZGE37 contained a BamHI site, whereas ZGE38 and ZGE39 contained an EcoRI site. PCR products were amplified from pBKHpfucT31 with a primer pair of either ZGE37/ZGE38 or ZGE37/ZGE39. These PCR-amplified DNA fragments were digested with EcoR1 and BamH1, and then cloned into pBluescript II KS-(Stratagene, La Jolla, CAS). The respective clones containing the H. pylori fucT gene of interest were screened by PCR with the corresponding pair of the above primers. Two clones, designated pBKHp763fucT38 and pBKHp763fucT39, contained a partial and an intact H. pylori fucT gene respectively. The coding region of the H. pylori fucT gene was controlled under the T7 promoter. The sequence of the PCR-amplified DNA fragments in pBKHp763fucT38 and pBKHp763fucT39 was determined and demonstrated to be identical to that of the native template.

Recombinant plasmids pBKHp763fucT38 and pBKHp763fucT39 were introduced into E. coli CSRDE3 cells by electroporation. The proteins encoded by the recombinant plasmids were over expressed in the presence of either [$^{35}$S]methionine or cold methionine. The cells expressing [$^{35}$S]methionine-labeled proteins were boiled for 5 min in 1 X sample buffer and separated in a 13.5% SDS-polyacrylamide gel.

EXAMPLE 3
Fucosyltransferase Assays

E. coli CSRDE3 cells expressing nonradioactively labeled proteins encoded by pBKHp763fucT38 and pBKHp763fucT39 were harvested and suspended in Hepes buffer (20 mM Hepes, pH 7.0) supplemented with 0.5 mM of phenylmethylsulfonic fluoride (a proteinase inhibitor). Subsequently, membrane and soluble fractions of the cells were prepared after disruption with a French press. The membrane pellets were resuspended in the same Hepes buffer, frozen in liquid nitrogen, and stored at −70° C. until use.

Assays of H. pylori α1,3 and α1,4 fucosyltransferase activities were conducted at 37° C. for 20 min in a volume of 20 μl containing either 720 μM LacNAc-R for α1,3-fucosyltransferase activity, Galβ1–3GlcNAc-R for α1,4-fucosyltransferase activity, or 5.33 mM Phenyl-Gal for α1,2-fucosyltransferase activity, 50 μM GDP-fucose, 100,000 d.p.m GDP-[$^3$H]fucose, 20 mM Hepes buffer (pH 7.0), 20 mM MnCl$_2$, 0.2% BSA and 8.5 μl of the enzyme fraction. The incubation mixtures were loaded onto Sep-Pak Plus C-18 cartridges and the unreacted donor was removed by washing the cartridges with water. The reaction products were eluted from the cartridges with 4 ml of methanol, and radioactivity was counted in 10 ml of Ecolite (+) cocktail in a Beckman LS 1801 scintillation counter (Palcic, M. M., Venot, A. P., Ratcliffe, R. M., and Hindsaul, O. (1988) Carbohydr. Res. 190, 1–11).

Capillary Electrophoresis Assay

The incubation mixtures contained 16 μl of the membrane fraction containing the intact HpFucT protein, 100 μM LacNAc-TMR, 100 μM GDP-fucose in a total volume of 20 μl of 20 mM Hepes (pH 7.0) containing 20 mM MnCl2 and 0.2% BSA. Incubation was done at 37° C. for 30 minutes. Subsequently, the sample was prepared and analyzed by capillary electrophoresis by injecting 12 μl onto an electrophoresis column (60 cm long) at 1 kV for 5 s. The electrophoretic separations were performed at a running voltage of 400 V/cm. α-Fucosidase treatment was done by incubating the sample (10 mM total TMR) with 4 mU almond meal α-fucosidase (Sigma-Aldrich, Canada, Ltd, Misissauga, Ontario) in a total volume of 40 μl of 50 mM sodium citrate buffer, pH 5.0 at 37° C. for 90 hours. Products were isolated and analyzed by capillary electrophoresis as described above.

RESULTS

Cloning and Nucleotide Sequence of a *H. pylori* Fucosyltransferase Gene

Three recombinant plasmids, pCRHpfucT3, pBKHpfucT8 and pBKHpfucT31 (FIG. 1) containing the intact or partial sequence of the fucT gene from *H. pylori* NCTC11639, were obtained as described in the examples above. The nucleotide sequences of these recombinant clones were sequenced from both strands using nested primers. FIG. 2A shows a nucleotide sequence of 1670 bp derived from clone pBKHpfucT31. The sequence is characterized by a major open reading frame (ORF), starting at nucleotide 145 and ending at nucleotide 1356, which was predicted in this region. As shown in FIG. 2A, an unusual sequence feature of this ORF was eight direct repeats of 21 nucleotides. An AA to GG transition at positions 12 and 13 of this repeat has occurred in repeat copies III and VI. An SD sequence, a ribosomal binding site (RSB) in prokaryotes (Shine, J., and Dalgarno, L. (1974) *Proc. Natl. Acad. Sci. USA* 71 1342–1346), precedes the predicted translation initiation codon AUG. In addition, the sequence "ACCATGT", which is similar to the Kozak's consensus context "ACCATGG" (a common RSB in eukaryotes) (Kozak, M. (1986) *Cell* 44, 229–292), also exists at the beginning of the ORF. Putative transcription elements including –10 and –35 regions immediately upstream of the ORF, and a stem-loop structure following the stop codon of the ORE, which probably act as a transcription promoter and rho-independent transcription terminator (Platt, T. (1986) *Annu. Rev. Biochem.* 55, 339–372), were identified. An asymmetric inverted repeat sequence was found, encompassing 18 nucleotides and containing the putative –10 region. Another ORF downstream from the major ORF, in the opposite orientation as indicated in FIG. 2A, encodes the amino acid sequence similar to the corresponding region of the glutamate dehydrogenase identified in *Corynebacterium glutamicum* (nucleotide sequence accession #S32227).

Features of the Deduced Amino Acid Sequence of the *H. pylori* fucT

A protein consisting of 464 amino acids with a calculated molecular mass of 54,429 daltons was predicted from this ORF. A hydropathy profile (FIG. 2B) which was calculated by the method of Kyte and Doolittle ((1982) *J. Mol. Biol.* 157, 105–132), indicates that the deduced amino acid sequence is primarily hydrophilic, and does not contain a potential transmembrane segment ("transmembrane segment-free").

Additionally, the predicted protein from the NTCT11639 *H. pylori* strain carries eight direct repeats of seven amino acid residues proximal to the C-terminus. There is a conservative replacement of valine by isoleucine at position 5 found in repeats III and VI, which results from the corresponding AA to GG mutations as mentioned above. Cloning of a number HpFucT from additional strains of *H. pylori* have demonstrated that the amino acid sequence is highly conserved (77% identity and 87% similarity) except for the heptad repeats. *H. pylori* contains two copies of HpFucT. The number of heptad repeats which potentially constitute a leucine zipper (L-Zip) domain are highly variable among the HpFucTs cloned and range from 11 to 3 in the various strains of *H. pylori*. (FIG. 6) There are some substitutions introduced into the heptad repeats. The repeat unit in UA1182 *H. pylori* strain is "DDLRVNY" (SEQ ID NO:25), whereas in the UA802 strain the repeat unit is "NNLRADY" (SEQ ID NO:26). (FIG. 6) Searches for sequence similarly shown in FIG. 3B revealed that this region of repeats in HpFucT is significantly similar to domains potentially forming a leucine-zipper structure within several homeobox-leucine zipper proteins (HD-Zip protein) including ATHB-1, ATHB-5, 6 (SEQ ID NO:16), and 7 (SEQ ID NO:18) from *Arabidoposis thaliana* and tomato (nucleotide sequence accession #x94947) (FIG. 3B). The conserved leucine residues are also colinear to those present in the leucine zipper motif found in a group of basic region-leucine zipper (bZip) proteins in eukaryotes, including yeast, higher plant, animals, and recently, in a bacterium.

Five putative N-linked glycosylation sites are predicted, two of which are proximal to the N-terminus, similar to those identified in mammalian FucTs. However, the remaining three such sites are close to the C-terminus. This latter feature is similar to the sites identified in rabbit and human α1,2-fucosyltransferases (Hitoshi, S., Kusunoki, S., Kanazawa, I., and Tsuji, S. (1996) *J. Biol. Chem.* 264, 17615–17618). Comparison of this polypeptide sequence with other proteins in the protein data bases, using the Blast search program (Version 8.0, Genetic Computing Group, Inc., Madison, Wis.) revealed significant sequence similarity (40–45% identity) to α1–3 and 1–3/1–4 fucosyltransferases from mammalian sources, including human FucT III to VII, bovine FucT III and CFT1 from chicken within an approximately 72 amino acid stretch. As denoted in FIG. 3A, this region is located in the proposed C-terminal catalytic domains of FucTs. Therefore, we designated this gene as HpfucT.

The remaining sequence beyond this conserved region is relatively divergent from that of eukaryotic FucTs. HpFucT appears to lack the transmembrane segment that is common to eukaryotic FucTs, and which is usually located in their N-terminal region. On the other hand, eukaryotic FucTs do not contain the ~100 aa region encompassing eight "DDLRV(or I)NY" (SEQ ID NO:27) repeats.

Characterization of the HpfucT Gene Product in *E. coli* Cells

Figure 4:
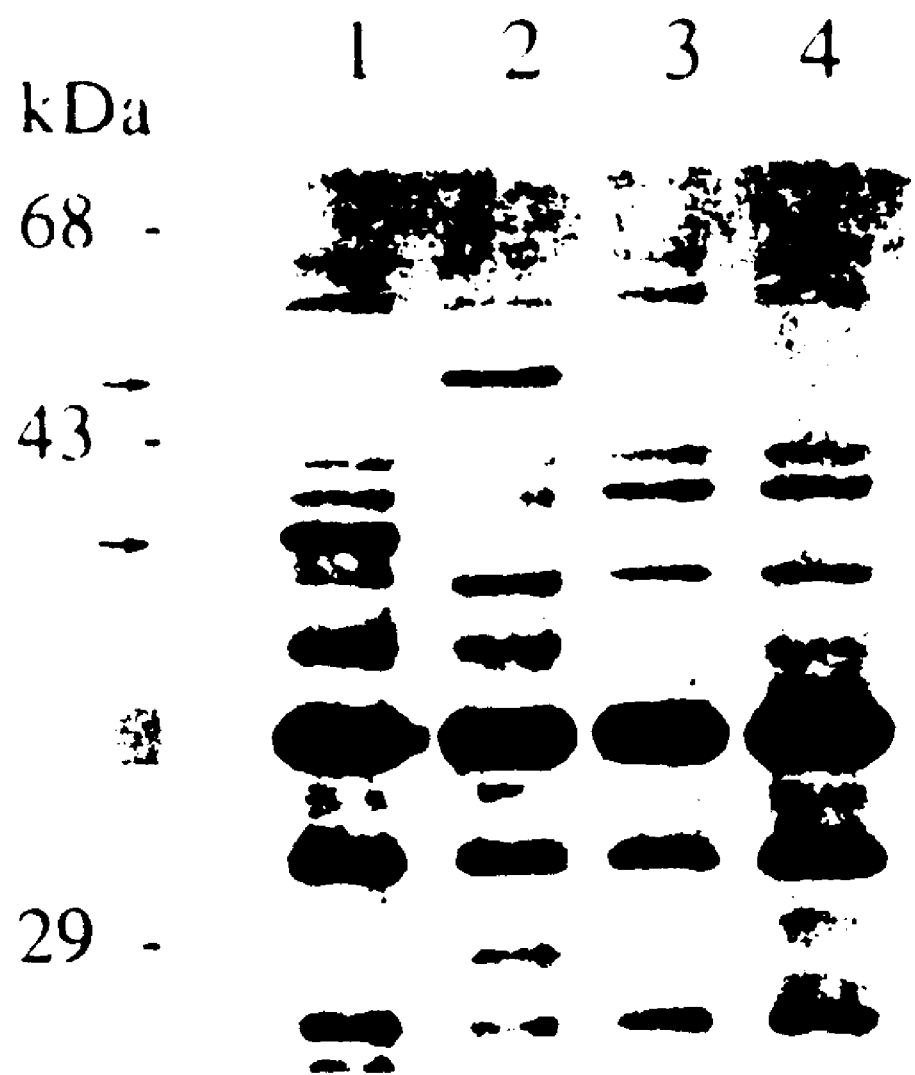
FIG. 4 is a electrophoresis gel showing over expression of the *H. pylori* fucT gene in *E. coli* CSRDE3 cells. Equal amounts of the protein extracts as determined by the turbidity of the cultures were separated on a 13.5% polyacrylamide gel. Lane 1, pBKHp763fucT38; Lane 2, pBKHp763fucT39; Lane 3, pBluescript II KS-; Lane4, no plasmid. The proteins bands of interest and molecular mass makers (BRL/Gibco) were indicated by arrow heads and lines on the left, respectively.

To investigate whether or not the predicted HpFucT gene represents a complete locus, a maxicell system was used to detect the protein encoded by this gene. A modified CSR603 strain, which carries a Plac-controlled T7 DNA polymerase gene on the chromosome, was applied for the HpfucT expression. Two recombinant plasmids, pBKHp763fucT38 (carrying the partial HpFucT gene) and pBKHp763fucT39 (carrying the intact HpfucT gene), were constructed (FIG. 1). The HpfucT genes in these two plasmids were controlled by a T7 promoter. Results of expression from these plasmids are shown in FIG. 4. pBKHp763fucT39 gave rise to a specific product of ~52 kDa (FIG. 4, lane 2) which is in agreement of the predicted molecular mass of 54 kDa. In addition, a protein of ~41 kDa was produced from pBKHp763fucT38-containing cells (FIG. 4, lane 1). The size of this product is consistent with the predicted 42 kDa of the truncated HpFucT in which the C-terminal 101 amino acids of HpFucT were removed. In contrast, these HpFucT-encoded proteins were not produced in control cells containing either no plasmid or a vector without the insert (FIG. 4, lanes 4 and 3, respectively). Two strong bands at ~35 kDa and 29 kDa were present in all the samples, indicating that they were encoded by host genes. This evidence demonstrates that the cloned HpfucT represents a complete locus.

Biochemical Assay of the Overproduced HpFucT Protein

The partial sequence of this bacterial FucT is homologous to the catalytic domain of mammalian FucTs, suggesting that HpFucT is a fucosyltransferase. Therefore, the nature of this enzyme activity was investigated. To delineate the cellular location of the enzyme activity, membrane and cytoplasmic fractions of *E. coli* cells producing the HpFucT proteins were prepared. The α1,3-HpFucT activity was quantitated using LacNAc-R as an acceptor and GDP-fucose as the donor. Approximately 85% of the total enzyme activity was associated with the membrane fraction containing the intact HpFucT protein expressed from pBKHp763fucT39; whereas the remaining portion was present in the cytoplasmic fraction (Table 1). No detectable activity of either α1,2-FucT or α1,4-FucT was found in the samples tested.

Figure 5A:
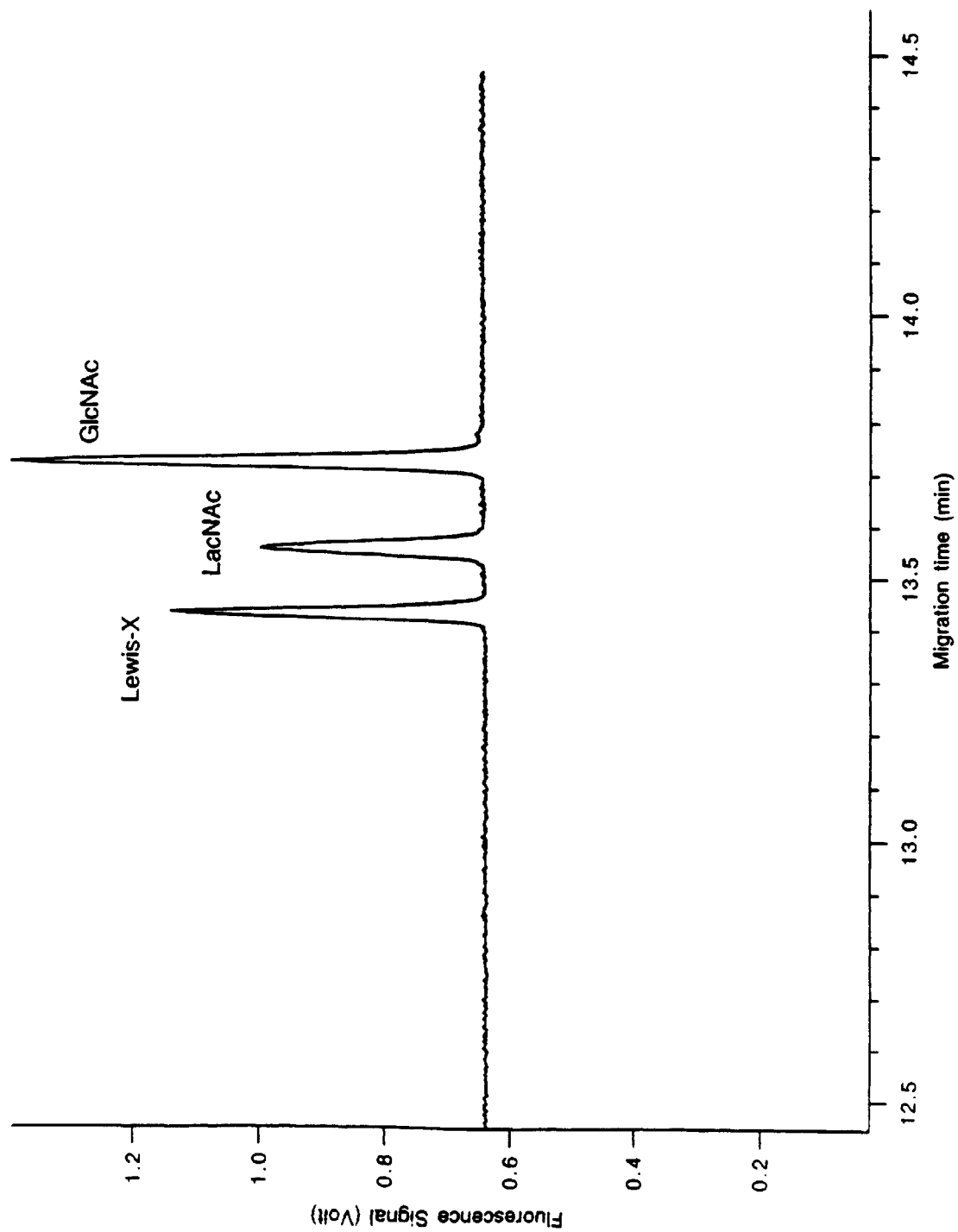
FIG. 5A is an electropherogram showing the reaction product from an incubation containing LacNAc-TMR and GDP-fucose with the membrane extract from pBKHp763fucT39. Lewis X (Galβ1→4[Fucα1→3]GlcNAcβ-TMR) and GlcNAcβ-TMR were formed and confirmed by both co-injection with standards and treatment with a-fucosidase.
Figure 5B:
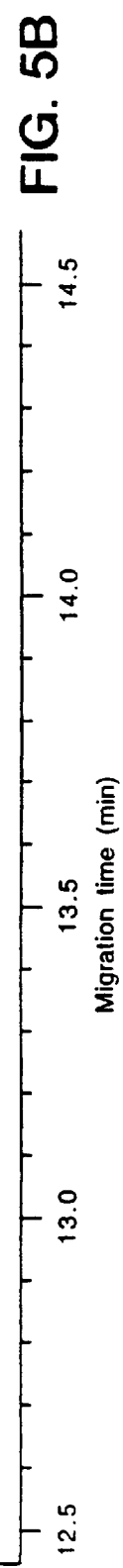
FIG. 5B is an electropherogram showing the reaction mixture obtained from a-fucosidase treatment containing Lewis-X-TMR with a 36% reduction in fluorescence signal. The GlcNAc-TMR peak also had a corresponding increase in intensity by 39%.

The Triton X-100-solubilized membrane fraction gave rise to slightly higher α1,3-FucT activity than the untreated extract (Table 1). No α1,3-FucT activity was obtained from either the membrane or the cytoplasmic fractions prepared from cells producing the truncated HpFucT protein encoded by pBKHp763fucT38. This result indicated that the C-terminal 101 aa of HpFucT is crucial for fucosyltransferase activity. The reaction products synthesized by the *H. pylori* α1,3 fucosyltransferase were characterized using capillary electrophoresis with laser-induced fluorescence detection of tetramethylrhodamine (TMR)-labeled acceptors as described in according to a known method. The capillary was 60 cm long (10 μm i.d.), and the samples were injected onto the electrophoresis column at 1 kV for 5 seconds. The running buffer was 10 mM in phosphate, borate, phenylboronic acid, and SDS (pH 9.3); the running voltage was 400 V/cm. The reaction mixture containing the membrane fraction of cells harboring pBKHp763fucT39, GDP-fucose, and LacNAC-TMR produced a new peak (FIG. 5a, Lewis-X peak), which co-migrated with a synthetic $Le^x$-TMR in the electropherogram (FIG. 5c, peak 3), indicating that the new peak represents a $Le^x$ product synthesized by the bacterial α1,3-fucosyltransferase of this invention. Synthesis of $Le^x$ with this enzyme was further tested by digestion of $Le^x$ with fucosidase, which cleaved the $Le^x$ product and released LacNAc-TMR. Electrophoresis of the reaction mixture demonstrated that the concentration of LacNAc in the reaction mixture increased by 39%(FIG. 5b, LacNAc peak); whereas the concentration of the $Le^x$ product decreased by 36% (FIG. 5b, $Le^x$ peak), showing that the test product was synthesized by fucosyltransferase activity. FIG. 5C shows separation of nine standard TMR oligosaccharides found in mammalian metabolism, LacNAcb- (1), Fucα1→2Galβ1→4GlcNAcβ- (2), Galβ1→4[Fucα1→3]GlcNAcβ- (3), Fucα1→2Galβ1→4[Fucα1→3]GlcNAcβ- (4), GlcNAcβ- (5), linker arm- (6), NeuAcα2→6LacNAcβ- (7), NeuAcα2→3LacNAcβ- (8), NeuAcα2→3Galβ1→4[Fucα1→3]GlcNAcβ-TMR (9).

What is claimed is:

1. An isolated polynucleotide encoding an amino acid sequence of SEQ ID NO:1, its complement, or a fragment thereof having α1,3 fucosyltransferase activity.

2. An isolated polynucleotide selected from the group consisting of:
   a) SEQ ID NO: 4
   b) SEQ ID NO: 4, wherein T is U; and
   c) nucleic acid sequences complementary to a) or b).

3. An isolated polynucleotide encoding an amino acid sequence of SEQ ID NO:2, its complement, or a fragment thereof having α1,3-fucosyltransferase.

4. An isolated polynucleotide encoding an amino acid sequence of SEQ ID NO:3, its complement, or a fragment thereof having α1,3-fucosyltransferase.

5. A vector containing the polynucleotide of any one of claims 1–4.

6. A host cell containing the vector of claim 5.

7. A recombinant method for producing an α1,3-fucosyltransferase polypeptide fused to a selectable marker, comprising:
   inserting the polynucleotide of any one of claims 1–4 adjacent to a selectable marker, such that the resulting polynucleotide encodes a recombinant polypeptide having α1,3-fucosyltransferase activity fused to the selectable marker; and expressing the resulting polynucleotide to produce a polypeptide having α1,3-fucosyltransferase activity fused to a selectable marker.

8. A polynucleotide produced by the method of claim 7.

9. A host cell containing the polynucleotide of claim 8.

10. A recombinant method for producing an α1,3-fucosyltransferase polypeptide, comprising:

a) growing a recombinant host cell containing the polynucleotide of any one of claims 1–4 under conditions which allow expression and secretion of a polypeptide having α1,3-fucosyltransferase activity; and b) isolating the polypeptide.

11. A method of producing an α1,3-fucosyltransferase fusion protein comprising:

a) growing a host cell containing the polynucleotide of any one of claims 1–4 encoding a polypeptide having α1,3-fucosyltransferase activity operably linked to a polynucleotide encoding a polypeptide or peptide of interest under conditions which allow expression and secretion of the fusion protein; and b) isolating the fusion protein.

12. A gene expression system for producing an α1,3-fucosyltransferase comprising a host cell transformed with the polynucleotide of any one of claims 1–4 encoding a polypeptide having α1,3-fucosyltransferase activity.

13. The gene expression system of claim 12, wherein the polynucleotide is DNA.

14. The gene expression system of claim 12, wherein the polynucleotide is cDNA.

15. The gene expression system of claim 12, wherein the polynucleotide is RNA.

16. The gene expression system of claim 12, wherein the host cell is selected from the group consisting of a bacterial cell, a yeast cell, a fungal cell, a plant cell and an animal cell.

17. The gene expression system of claim 12, wherein the host cell is recombinantly modified by transfection with a plasmid.

18. The gene expression system of claim 17, wherein the plasmid comprises a selectable marker.

19. The gene expression system of claim 18, wherein the selectable marker is glutamine synthetase.

20. A method for producing an α1,3-fucosyltransferase polypeptide, comprising the steps of:

(a) providing a gene expression system of claim 12;

(b) expressing the polypeptide; and (c) harvesting the α1,3-fucosyltransferase polypeptide.

21. The method of claim 20, further comprising substantially purifying the harvested α1,3-fucosyltransferase polypeptide.

22. An isolated polynucleotide comprising the nucleic acid sequence as set forth in SEQ ID NO:4.

* * * * *